(12) United States Patent
Mardor et al.

(10) Patent No.: US 8,391,959 B2
(45) Date of Patent: *Mar. 5, 2013

(54) COMPOSITION FOR IMPROVING EFFICIENCY OF DRUG DELIVERY

(75) Inventors: Yael Mardor, Netania (IL); Zvi Ram, Ramat-Gan (IL)

(73) Assignees: Tel HaShomer Medical Research Infrastructure and Services Ltd., Ramat-Gan (IL); Medical Research Fund of Tel Aviv Sourasky Medical Center, Tel-Aviv (IL)

( * ) Notice: Subject to any disclaimer, the term of this patent is extended or adjusted under 35 U.S.C. 154(b) by 950 days.

This patent is subject to a terminal disclaimer.

(21) Appl. No.: 11/664,126

(22) PCT Filed: Sep. 29, 2005

(86) PCT No.: PCT/IL2005/001049
§ 371 (c)(1),
(2), (4) Date: Mar. 25, 2009

(87) PCT Pub. No.: WO2006/035444
PCT Pub. Date: Apr. 6, 2006

(65) Prior Publication Data
US 2009/0208422 A1    Aug. 20, 2009

Related U.S. Application Data

(60) Provisional application No. 60/613,720, filed on Sep. 29, 2004, provisional application No. 60/613,721, filed on Sep. 29, 2004, provisional application No. 60/623,878, filed on Nov. 2, 2004, provisional application No. 60/677,813, filed on May 5, 2005, provisional application No. 60/677,827, filed on May 5, 2005.

(51) Int. Cl.
*A61M 25/00*   (2006.01)
*A61M 5/14*    (2006.01)
*A61B 5/055*   (2006.01)

(52) U.S. Cl. .................. 600/433; 604/506; 424/9.3

(58) Field of Classification Search .............. None
See application file for complete search history.

(56) References Cited

U.S. PATENT DOCUMENTS

| | | |
|---|---|---|
| 4,183,011 A | 1/1980 | Massa |
| 4,211,489 A | 7/1980 | Kleinknecht et al. |
| 4,271,490 A | 6/1981 | Minohara et al. |
| 4,297,607 A | 10/1981 | Lynnworth et al. |
| 4,433,399 A | 2/1984 | Massa |
| 4,452,081 A | 6/1984 | Seppi |
| 4,501,186 A | 2/1985 | Ikuma |
| 4,554,834 A | 11/1985 | Prinz et al. |
| 4,576,047 A | 3/1986 | Lauer et al. |
| 4,577,506 A | 3/1986 | Poole et al. |
| 4,630,072 A | 12/1986 | Scardovi et al. |
| 4,641,291 A | 2/1987 | Simmons et al. |
| 4,672,592 A | 6/1987 | Skinner |
| 4,814,552 A | 3/1989 | Stefik et al. |
| 4,991,148 A | 2/1991 | Gilchrist |
| 5,062,089 A | 10/1991 | Willard et al. |
| 5,138,159 A | 8/1992 | Takase et al. |
| 5,142,506 A | 8/1992 | Edwards |
| 5,202,231 A | 4/1993 | Drmanac et al. |
| 5,245,863 A | 9/1993 | Kajimura et al. |
| 5,372,138 A | 12/1994 | Crawley et al. |
| 5,391,197 A | 2/1995 | Burdette et al. |
| 5,394,741 A | 3/1995 | Kajimura et al. |
| 5,421,338 A | 6/1995 | Crowley et al. |
| 5,432,346 A | 7/1995 | Nose et al. |
| 5,433,717 A | 7/1995 | Rubinsky et al. |
| 5,492,806 A | 2/1996 | Drmanac et al. |
| 5,511,043 A | 4/1996 | Lindberg |
| 5,515,853 A | 5/1996 | Smith et al. |
| 5,517,579 A | 5/1996 | Baron et al. |
| 5,519,686 A | 5/1996 | Yanagisawa et al. |
| 5,524,630 A | 6/1996 | Crowley |
| 5,525,464 A | 6/1996 | Drmanac et al. |
| 5,530,683 A | 6/1996 | Lindberg |
| 5,550,791 A | 8/1996 | Peloquin et al. |
| 5,588,432 A | 12/1996 | Crowley |
| 5,657,760 A | 8/1997 | Ying et al. |
| 5,667,972 A | 9/1997 | Drmanac et al. |
| 5,682,445 A | 10/1997 | Smith |
| 5,695,940 A | 12/1997 | Drmanac et al. |
| 5,702,629 A | 12/1997 | Cui et al. |
| 5,715,825 A | 2/1998 | Crowley |
| 5,720,720 A * | 2/1998 | Laske et al. .................... 604/500 |
| 5,721,721 A | 2/1998 | Yanagisava et al. |
| 5,840,031 A | 11/1998 | Crowley et al. |
| 5,866,856 A | 2/1999 | Holtzman |
| 5,895,356 A | 4/1999 | Andrus et al. |

(Continued)

FOREIGN PATENT DOCUMENTS

| | | |
|---|---|---|
| EP | 0312481 | 4/1989 |
| EP | 0666543 | 8/1995 |

(Continued)

OTHER PUBLICATIONS

Mardor et al (Proc Intl Soc Mag Reson Med, 2001, 9:145).*

(Continued)

*Primary Examiner* — Laura B Goddard

(57) ABSTRACT

Method and composition suitable for administering by direct convective interstitial infusion are disclosed. The method comprises: placing at least one direct convective interstitial infusion catheter in contact with the tissue, and pressuring the composition through the catheter. The composition is in a liquefied form having a viscosity above a predetermined value. The predetermined value is selected so as to improve infusion of the compositions into interstitial volumes of the tissue, while minimizing backflow of the compositions along an outer wall of the catheter or leakage into low resistance paths. It is demonstrated that high viscosity results in higher treatment efficiency.

44 Claims, 23 Drawing Sheets
(19 of 23 Drawing Sheet(s) Filed in Color)

U.S. PATENT DOCUMENTS

| | | | |
|---|---|---|---|
| 5,972,619 A | 10/1999 | Drmanac et al. |
| 5,977,958 A | 11/1999 | Baron et al. |
| 6,004,269 A | 12/1999 | Crowley et al. |
| 6,018,041 A | 1/2000 | Drmanac et al. |
| 6,025,136 A | 2/2000 | Drmanac |
| 6,026,316 A | 2/2000 | Kucharczyk et al. |
| 6,050,943 A | 4/2000 | Slayton et al. |
| 6,111,565 A | 8/2000 | Chery et al. |
| 6,137,621 A | 10/2000 | Wu |
| 6,147,681 A | 11/2000 | Chery et al. |
| 6,151,014 A | 11/2000 | Zloter et al. |
| 6,169,281 B1 | 1/2001 | Chen et al. |
| 6,211,863 B1 | 4/2001 | Chery et al. |
| 6,232,962 B1 | 5/2001 | Davis et al. |
| 6,252,656 B1 | 6/2001 | Wu et al. |
| 6,265,676 B1 | 7/2001 | Zloter et al. |
| 6,268,210 B1 | 7/2001 | Baler et al. |
| 6,270,961 B1 | 8/2001 | Drmanac |
| 6,282,340 B1 | 8/2001 | Nasu et al. |
| 6,292,177 B1 | 9/2001 | Zloter et al. |
| 6,292,180 B1 | 9/2001 | Lee |
| 6,297,006 B1 | 10/2001 | Drmanac et al. |
| 6,298,259 B1 | 10/2001 | Kucharczyk et al. |
| 6,300,076 B1 | 10/2001 | Koster |
| 6,300,580 B1 | 10/2001 | Shenholtz et al. |
| 6,309,824 B1 | 10/2001 | Drmanac |
| 6,316,191 B1 | 11/2001 | Drmanac et al. |
| 6,367,335 B1 | 4/2002 | Hicks |
| 6,383,742 B1 | 5/2002 | Drmanac et al. |
| 6,392,230 B1 | 5/2002 | Aita |
| 6,392,330 B1 | 5/2002 | Zloter et al. |
| 6,401,267 B1 | 6/2002 | Drmanac |
| 6,403,315 B1 | 6/2002 | Drmanac |
| 6,424,340 B1 | 7/2002 | Holtzman et al. |
| 6,430,342 B1 | 8/2002 | Kim et al. |
| 6,451,015 B1 | 9/2002 | Rittman, III et al. |
| 6,451,996 B1 | 9/2002 | Drmanac et al. |
| 6,461,641 B1 * | 10/2002 | Fick | 424/489 |
| 6,480,791 B1 | 11/2002 | Strathmann |
| 6,485,413 B1 | 11/2002 | Boppart et al. |
| 6,500,121 B1 | 12/2002 | Slayton et al. |
| 6,504,289 B2 | 1/2003 | Toda et al. |
| 6,508,774 B1 | 1/2003 | Acker et al. |
| 6,537,755 B1 | 3/2003 | Drmanac |
| 6,577,299 B1 | 6/2003 | Schiller et al. |
| 6,681,635 B1 | 1/2004 | Van Schaik |
| 6,716,184 B2 | 4/2004 | Vaezy et al. |
| 6,724,371 B1 | 4/2004 | Shenholtz et al. |
| 6,738,408 B2 | 5/2004 | Abedin |
| 6,745,632 B1 | 6/2004 | Dryer et al. |
| 6,771,006 B2 | 8/2004 | Zloter et al. |
| 6,778,735 B2 | 8/2004 | Miller et al. |
| 6,816,266 B2 | 11/2004 | Varshneya et al. |
| 6,822,641 B2 | 11/2004 | Shenholtz et al. |
| 6,823,105 B2 | 11/2004 | Zloter et al. |
| 6,831,781 B2 | 12/2004 | Tearney et al. |
| 6,841,742 B2 | 1/2005 | Shenholtz et al. |
| 6,873,415 B2 | 3/2005 | Amonette et al. |
| 7,367,944 B2 | 5/2008 | Rosemberg et al. |
| 7,371,225 B2 | 5/2008 | Oldfield et al. |
| 2002/0031243 A1 | 3/2002 | Schiller et al. |
| 2002/0052311 A1 | 5/2002 | Solomon et al. |
| 2003/0095708 A1 | 5/2003 | Pittel |
| 2003/0142065 A1 | 7/2003 | Pahlavan |
| 2004/0032399 A1 | 2/2004 | Sekiguchi et al. |
| 2004/0106870 A1 | 6/2004 | Mast |
| 2004/0267120 A1 | 12/2004 | Podany et al. |
| 2005/0150697 A1 | 7/2005 | Altman et al. |
| 2008/0132792 A1 | 6/2008 | Rosemberg et al. |

FOREIGN PATENT DOCUMENTS

| | | |
|---|---|---|
| EP | 1450296 | 8/2004 |
| EP | 1504330 | 8/2006 |
| GB | 2043899 | 10/1980 |
| GB | 2121174 | 12/1983 |
| TW | 394833 | 6/2000 |
| WO | WO 00/21203 | 4/2000 |
| WO | WO 01/35329 | 5/2001 |
| WO | WO 02/01466 | 1/2002 |
| WO | WO 03/069547 | 8/2003 |
| WO | WO 03/088136 | 10/2003 |
| WO | WO 2004/010592 | 1/2004 |
| WO | WO 2004/031348 | 4/2004 |
| WO | WO 2004/076683 | 9/2004 |
| WO | WO 2005/111653 | 11/2005 |
| WO | WO 2006/035444 | 4/2006 |
| WO | WO 2006/035443 | 6/2006 |
| WO | WO 2006/064495 | 6/2006 |
| WO | WO 2006/100682 | 9/2006 |

OTHER PUBLICATIONS

Lonser et al (J Neurosurgery, 2002, 97:905-913).*
International Preliminary Report on Patentability Dated Jun. 21, 2007 From the International Bureau of WIPO Re.: Application No. PCT/IL2005/001337.
International Preliminary Report on Patentability Dated Jan. 22, 2009 From the International Bureau of WIPO Re.: Application No. PCT/IL2005/001048.
Official Action Dated Mar. 17, 2009 From the US Patent and Trademark Office Re.: U.S. Appl. No. 12/068,621.
Attisano et al. "Signal Transduction by the TGF-$\beta$ Superfamily", Science, 296(5573): 1646-1647, 2002.
Nicolet et al. "Desulfovibrio Desulfuricans Iron Hydrogenase: The Structure Shows Unusual Coordination to an Active Site Fe Binuclear Center", Structure, 7: 13-23, 1999.
Nonaka et al. "Ultrasonic Position Measurement and Its Applications to Human Interface", Instrumentation and measurement Technology Conference, 1994, IMTC/94, Conference Proceedings, 10th Anniversary, Advanced Technologies in I & M, IEEE, Hamamatsu, Japan, p. 753-756, 1994.
Peters et al. "X-Ray Crystal Structure of the Fe-Only Hydrogenase (CpI) From Clostridium Pasteurianum to 1.8 Angstrom Resolution", Science, 282: 1853-1858, 1998.
Response Dated May 6, 2010 to Office Action of Nov. 8, 2009 From the Israel Patent Office Re.: Application No. 182321.
Response Dated May 10, 2010 to Official Action of Nov. 9, 2009 From the US Patent and Trademark Office Re.: U.S. Appl. No. 12/068,621.
Office Action Dated Jul. 27, 2010 From the Israel Patent Office Re.: Application No. 182321 and Its Translation Into English.
Response Dated Sep. 2, 2010 to Office Action of Jul. 27, 2010 From the Israel Patent Office Re.: Application No. 182321.
Office Action Dated Aug. 29, 2010 From the Israel Patent Office Re. Application No. 182322 and Its Translation Into English.
Mardor et al. "Monitoring Response to Convection-Enhanced Taxol Delivery in Brain Tumor Patients Using Diffusion-Weighted Magnetic Resonance Imaging", Cancer Research, 61: 4971-4973, Jul. 1, 2001.
International Preliminary Report on Patentability Dated Dec. 26, 2006 From the International Preliminary Examining Authority Re.: Application No. PCT/IL05/01049.
International Search Report Dated Jul. 3, 2008 From the International Searching Authority Re.: Application No. PCT/IL05/01048.
International Search Report Dated May 9, 2006 From the International Searching Authority Re.: Application No. PCT/IL05/01049.
International Search Report Dated May 16, 2006 From the International Searching Authority Re.: Application No. PCT/IL05/01337.
Office Action Dated Nov. 8, 2009 From the Israel Patent Office Re.: Application No. 182321 and Its Translation Into English.
Official Action Dated Apr. 4, 2006 From the US Patent and Trademark Office Re.: U.S. Appl. No. 11/008,979.
Official Action Dated May 17, 2007 From the US Patent and Trademark Office Re.: U.S. Appl. No. 11/008,979.
Brix et al. "Regional Blood Flow, Capillary Permeability, and Compartmental Volumes: Measurement With Dynamic CT-Initial Experience", Radiology, 210: 269-276, 1999.
Croteau et al. "Real-Time in Vivo Imaging of the Convective Distribution of a Low-Molecular-Weight Tracer", The Journal of Neurosurgery, 102: 90-97, 2005.

Hori et al. "Circadian Variation of Tumor Blood Flow in Rat Subcutaneous Tumors and Its alteration by Angiotensin II-Induced Hypertension", Cancer Research, 52(4): 912-916, 1992. Abstract.

Phillips et al. "Acoustic Backscatter Properties of the Particle/Bubble Ultrasound Contrast Agent", Ultrasonics, 36(8): 883-892, 1998. Abstract.

Rhim et al. "Essential Techniques for Successful Radiofrequency Thermal Ablation of Malignant Hepatic Tumors", RadioGraphics, 21: S17-S39, 2001.

Response Dated Dec. 29, 2010 to Office Action of Aug. 29, 2010 From the Israel Patent Office Re. Application No. 182322.

Official Action Dated Apr. 12, 2011 From the US Patent and Trademark Office Re.: U.S. Appl. No. 12/068,621.

Official Action Dated Nov. 9, 2009 From the US Patent and Trademark Office Re.: U.S. Appl. No. 12/068,621.

Hori et al. "Circadian Variation of Tumor Blood Flow in Rat Subcutaneous Tumors and Its alteration by Angiotensin II-Induced Hypertension", Cancer Research, 52(4): 912-916, 1992. Abstract.

Cha et al. "CT Versus Sonography for Monitoring Radiofrequency Ablation in a Porcine Liver", American Journal of Roentgenology, 175: 705-711, 2000.

"Muon-Catalyzed Fusion", http://en.wikipedia.org/wiki/Muon-catalyzed_fusion, 2007.

Jackson "Catalysis of Nuclear Reactions Between Hydrogen Isotopes by μ-Mesons", Physical Review, 106(2): 330-339, 1957. Abstract.

Kimura et al. "Alpha-Muon Sticking and Chaos in Muon-Catalysed 'in Flight' D-T Fusion", arXiv: physics/0605206, 2: 1-8, 2006.

Nicolet et al. "Desulfovibrio Desulfuricans Iron Hydrogenase: The Structure Shows Unusual Coordination to an Active Site Fe Binuclear Center", Structure, 7: 13-.23, 1999.

Nonaka et al. "Ultrasonic Position Measurement and Its Applications to Human Interface", Instrumentation and Measurement Technology Conference, IMTC/94, Conference Proceedings, 10th Anniversary, Advanced Technologies in I & M, IEEE Hamatsu, Japan, IEEE New York, USA, p. 753-756, 1994.

Petrov "Muon Catalysis for Energy Production by Nuclear Fusion", Nature, 285: 466-468, 1980. Abstract.

Office Action Dated Nov. 6, 2011 From the Israel Patent Office Re.: Application No. 182321 and Its Translation Into English.

Saito et al. "Distribution of Liposomes Into Brain and Rat Tumor Models by Convection-Enhanced Delivery Monitored With Magentic Resonance Imaging", Cancer Research, 64: 2572-2579, Apr. 1, 2004.

Restriction Official Action Dated Apr. 11, 2012 From the US Patent and Trademark Office Re. U.S. Appl. No. 11/664,172.

\* cited by examiner

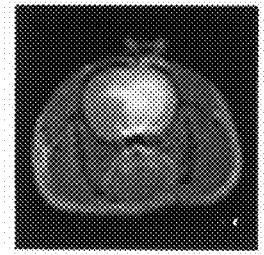 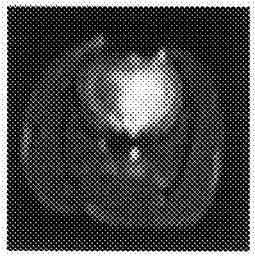
Fig. 4A          Fig. 4B
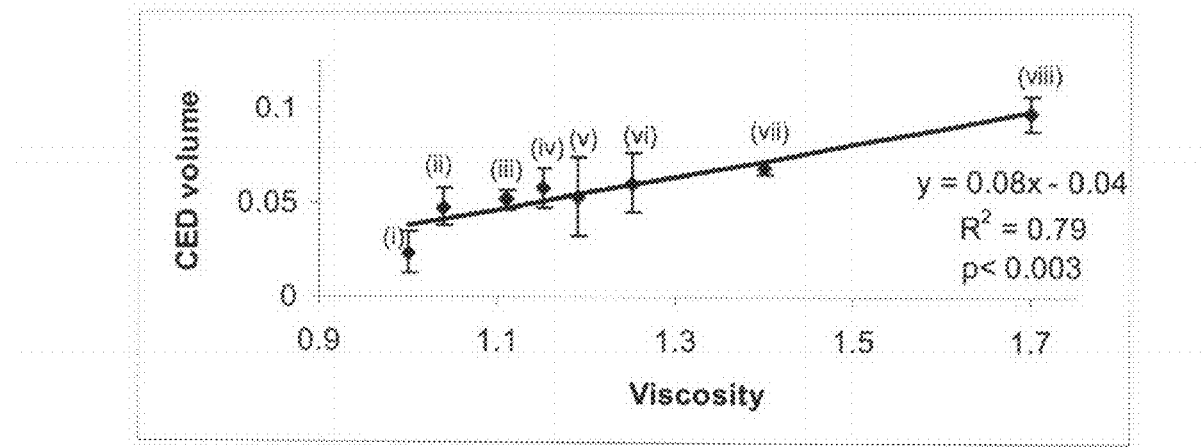
Fig. 5

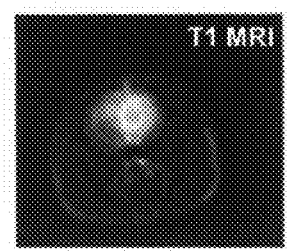
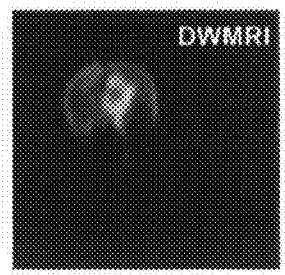
Fig. 9A    Fig. 9B
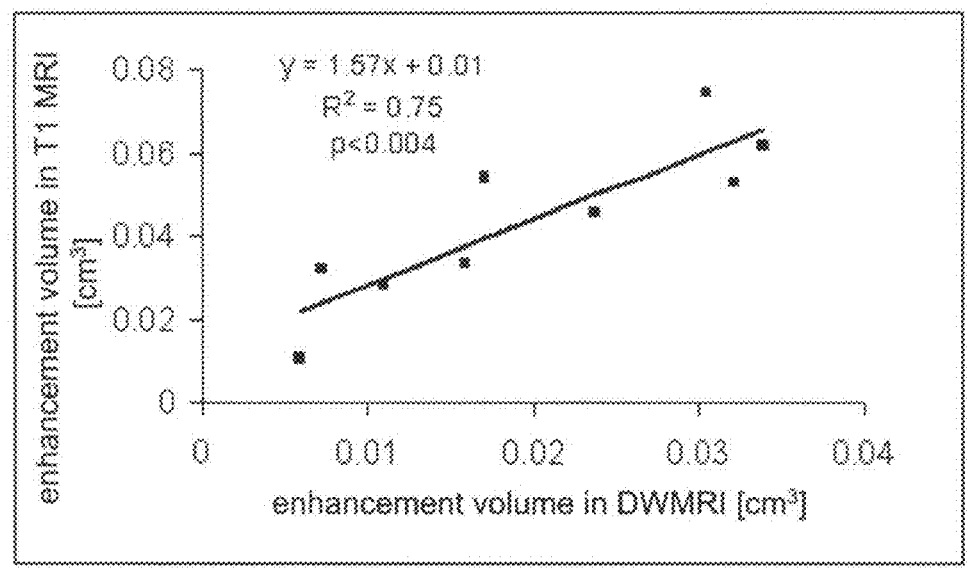
Fig. 9C

Fig. 23A 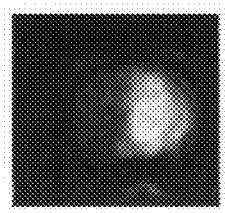 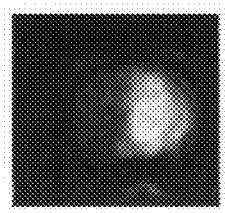 Fig. 23E
Fig. 23B 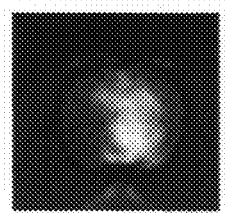 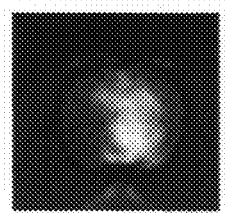 Fig. 23F
Fig. 23C 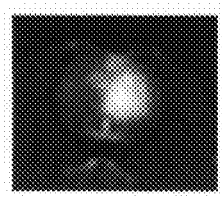 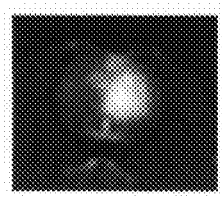 Fig. 23G
Fig. 23D 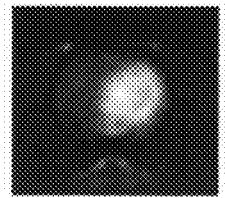 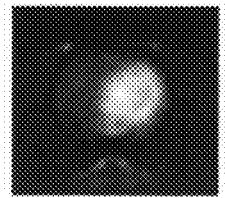 Fig. 23H

COMPOSITION FOR IMPROVING EFFICIENCY OF DRUG DELIVERY

RELATED APPLICATIONS

This Application is a National Phase of PCT Patent Application No. PCT/IL2005/001049 having International Filing Date of 29 Sep. 2005, which claims the benefit of U.S. Provisional Patent Application Nos. 60/677,813 filed on May 5, 2005, 60/677,827 filed on May 5, 2005, 60/623,878 filed on Nov. 2, 2004, 60/613,721 filed on Sep. 29, 2004 and 60/613,720 filed on Sep. 29, 2004. The contents of the above Applications are all incorporated herein by reference.

FIELD AND BACKGROUND OF THE INVENTION

The present invention relates to drug delivery and, more particularly, to a method and device for improving efficiency of convection-enhanced drug delivery.

In the area of drug delivery into the central nervous system (CNS), in particular for the treatment of neurological diseases, there have been extensive efforts for devising methods for delivering therapeutic agents into the desired neurological site. Peripheral administration of therapeutic agents for the treatment of CNS pathologies is mostly inefficient due to poor penetration of most drugs across the blood brain barrier (BBB). Direct drug delivery methods, such as direct injection, intracavitary instillation, intracavitary topical application, chronic low-flow microinfusion and controlled release from polymer implants, are restricted by the poor diffusion of drug through the tissue. Therefore, these drug delivery methods are only useful for treating a small volume of tissue surrounding the drug source.

Generally, diffusion of a compound in a tissue depends on the free concentration gradient and the diffusivity of the compound in the tissue. The diffusion in the tissue is slow for high molecular weight compounds, and higher for low molecular weight compounds. For the latter, however, capillary forces and oftentimes metabolism generally limit the diffusion efficiency and therapeutic drug levels can be obtained only close (a few millimeters) to the source of drug.

U.S. Pat. No. 5,720,720, the contents of which are hereby incorporated by reference, discloses a drug delivery technique known in the literature as "Convection-Enhanced Drug Delivery" and abbreviated to CED or CEDD. In this technique drugs delivery into the brain tumor is effected by application of pressure gradients (as opposed to concentration gradient). Specifically, CED involves positioning the tip of an infusion catheter within the brain tissue and supplying the drug through the catheter while maintaining a positive pressure gradient from the tip of the catheter during infusion. The catheter is connected to a pump which delivers the drug and maintains the desired pressure gradient throughout delivery of the drug. Drug delivery rates are typically about 0.5 to about 4.0 mcl/min with infusion distances of order of centimeters. This method is particularly useful for the delivery of drugs to solid nervous tissue.

In CED, fluid convection (bulk flow) in tissues occurs as a result of pressure gradients. Bulk flow of brain interstitial fluid occurs under normal conditions [Rosenberg G A, Kyner W T and Estrada E, "Bulk flow of brain interstitial fluid under normal and hyperosmolar conditions", Am. J. Physiol., 238: F42-F49, 1980], with vasogenic edema [Reulen H J, Graham R, Spatz M and Klatzo I "role of pressure gradients and bulk flow in dynamics of vasogenic brain edema", J. Neurosurg., 46:24-35, 1977] and after infusion of solutions directly into the brain parenchyma [Ohata K, Marmarou A, "Clearance of brain edema and macromolecules through the cortical extracellular space", J. Neurosurg., 77:387-396, 1992]. CED supplements diffusion and greatly enhances the distribution of small and large molecules in the brain [Bobo et al., "Convection-enhanced delivery of macromolecules in the brain," Proc. Natl. Asad. Sci. U.S.A., 91:2076-2080, 1994; Lieberman et al., "Convection-enhanced distribution of large molecules in gray matter during interstitial drug infusion", J. Neurosurg., 82:1021-1029, 1995].

CED is capable of obtaining in situ drug concentrations several orders of magnitude greater than those achieved by systemic administration. The concentration profile is relatively flat up to the flow front, providing control over undesired toxicity [Paul. F. Morrison, Douglas W Laske, Hunt Bobo. High-flow microinfusion: tissue penetration and pharmacodynamics. Am. J. Physiol. 266: 292-305, 1994].

In a phase II clinical trial in which patients were treated with CED of Tf-CRM107 (a conjugate protein of diphtheria toxin with a point mutation linked by a thioester bond to human transferrin) a significant antitumor response rate of 35% was reported [M. Weaver and D W Laske, "Transferrin receptor ligand-targeted toxin conjugate (Tf-CRM107) for therapy of malignant gliomas", J Neuro-Oncol 65:3-13, 2003]. Other drugs have also been tested in clinical trials with evidence of some clinical activity. Representative examples include TP-38 [Sampson et al., "Progress report of a phase I study of the intracerebral microinfusion of a recombinant chimeric protein composed of a transforming growth factor (TGF)-alpha and a mutated form of the pseudomonas exotoxin termed PE-38 (TP-38) for the treatment of malignant brain tumors", J Neuro-Oncol 65:27-35, 2003], and IL4(38-37)-PE38 KDEL [Kawakami et al., "Interleukin-4-pseudomonas exotoxin chimeric fusion protein for malignant glioma therapy", J Neuro-Oncol 65:15-25, 2003]. The use of IL13-PE38QQR resulted in no definite conclusive statements regarding efficacy [S R Husain and R K Puri, "Interleukin-13 receptor-directed cytotoxin for malignant glioma therapy: from bench to bedside", J Neuro-Oncol 65:37-48, 2003].

There are many variables affecting the convection, including the catheter size (narrow catheters are more efficient), flow rate (slow flow rates are more efficient), catheter localization [Lidar et al., "Convection-enhanced delivery of paclitaxel for the treatment of recurrent malignant glioma: a Phase I/II clinical study", Journal of Neurosurgery, 100: 472-479, 2004] and concentration and molecular weight of the infusate [Chen et al., "Variables affecting CED to the striatum: a systematic examination of rate of infusion, cannula size, infusate concentration, and tissue-cannula sealing time", J Neurosurg 90:315-320, 1999; Chen et al., "Intraparenchymal drug delivery via positive-pressure infusion: experimental and modeling studies of poroelasticity in brain phantom gels", IEEE Transactions on Biomedical Engineering, 49(2): 85-96, 2002]. Additionally, there is significant variability in differential tumor response to the therapeutic drugs, and in the extent of convection among patients and among different types of tissue. For example, convections tends to extend along low resistance paths, such as white matter tracks, necrosis, etc. Convection is also hampered when the treated region reaches regions of liquid accumulation, such as surgery site, sulci, ventricles etc. [Lidar et al., supra].

Moreover, presently known CED techniques are limited by the size of the administered molecule or particle. For molecule, the presently known upper limit is about 200 KDa and for liposomes the upper limit is less than 100 nm [Saito et al., "Distribution of liposomes into brain and rat brain tumor models by convection-enhanced delivery monitored with magnetic resonance imaging", Cancer Research, 1; 64(7): 2572-9, 2004; Mamot et al., "Extensive distribution of liposomes in rodent brains and brain tumors following convection-enhanced delivery", J Neurooncol 68(1):1-9, 2004].

There is thus a widely recognized need for, and it would be highly advantageous to have a composition for improving efficiency of convection-enhanced drug delivery.

SUMMARY OF THE INVENTION

According to one aspect of the present invention there is provided a method of administering a pharmaceutical agent to a tissue by direct convective interstitial infusion. The method comprises: placing at least one direct convective interstitial infusion catheter in contact with the tissue, and pressuring the pharmaceutical agent in a liquefied form having a viscosity above a predetermined value through the catheter. The predetermined value is preferably selected so as to improve infusion of the pharmaceutical agent into interstitial volumes of the tissue, while minimizing backflow of the pharmaceutical agent along an outer wall of the catheter, or along other low resistance paths near the target tissue.

According to another aspect of the present invention there is provided a method of formulating a pharmaceutical composition useful for direct convective interstitial infusion, the method comprises dissolving or dispersing a pharmaceutical agent in a pharmaceutical carrier so as to provide a pharmaceutical composition in a liquid form having a viscosity above a predetermined value selected as described herein.

According to further features in preferred embodiments of the invention described below, the method further comprises dissolving or dispersing a diagnostic agent in the pharmaceutical carrier.

According to yet another aspect of the present invention there is provided a pharmaceutical composition which comprises a pharmaceutical agent and a pharmaceutical carrier. The pharmaceutical composition is a liquefied form and has a sufficiently high viscosity selected as described herein.

According to yet a further aspect of the present invention there is provided a pharmaceutical composition, which comprises Taxol and a pharmaceutical carrier, the pharmaceutical composition is in liquid form, has a viscosity selected as described herein and is cremophor free.

According to further features in preferred embodiments of the invention described below, the composition comprises a pharmaceutical agent which can be a therapeutic and/or a diagnostic agent.

According to still further features in the described preferred embodiments the therapeutic agent comprises a gene therapy agent or a gene-related therapy agent.

According to still further features in the described preferred embodiments the therapeutic agent comprises a chemotherapeutic agent.

According to still further features in the described preferred embodiments the therapeutic agent comprises an anti-inflammatory agent.

According to still further features in the described preferred embodiments the therapeutic agent comprises an anti-pruritic agent, an anesthetic agent, an antimicrobial agent, an anti-oxidant, an antidepressant, a vitamin, an antihistamine, a hormone, an androgenic compound, a progestin compounds or a drug carrier for slow drug release or for targeting.

According to still further features in the described preferred embodiments the therapeutic agent has a molecular weight of at least 200 kDa.

According to still further features in the described preferred embodiments the pharmaceutical agent comprises a nanoparticle. According to still further features in the described preferred embodiments the nanoparticle comprises iron dioxide.

According to still further features in the described preferred embodiments the pharmaceutical agent in comprises a liposome.

According to still further features in the described preferred embodiments the diagnostic agent comprises an MRI contrast agent.

According to still further features in the described preferred embodiments the pharmaceutical agent is dissolved in the pharmaceutical carrier. According to still further features in the described preferred embodiments the pharmaceutical agent is suspended in the pharmaceutical carrier.

According to still another aspect of the present invention there is provided a method of preparing a pharmaceutical composition for direct convective interstitial infusion. The method comprises increasing a viscosity of the pharmaceutical composition to above a predetermined value selected as described herein. According to further features in preferred embodiments of the invention described below, the method further comprises dissolving or dispersing a diagnostic agent in the composition.

According to an additional aspect of the present invention there is provided a method of administering a pharmaceutical composition to a tissue by direct convective interstitial infusion, the pharmaceutical composition being in a liquid form. The method comprises: placing at least one direct convective interstitial infusion catheter in contact with the tissue; increasing a viscosity of the pharmaceutical composition above a predetermined value selected as described herein; and pressuring the pharmaceutical composition through the catheter.

According to still further features in the described preferred embodiments the increasing of the viscosity is by co-formulating the pharmaceutical composition with a pharmaceutical carrier having a viscosity above the predetermined value.

According to still further features in the described preferred embodiments the pharmaceutical carrier comprises an agent selected from the group consisting of serum albumin, sugars, ethanol, dextrane, polyethylene glycol, glycerol, dimethyl sulfoxide, corn oil and methanol.

According to still further features in the described preferred embodiments the viscosity is increased while keeping non-specific toxicity to a minimum.

According to still further features in the described preferred embodiments the method further comprises imaging a region containing the tissue by MRI thereby providing at least one image of the region.

According to yet an additional aspect of the present invention there is provided a direct convective interstitial infusion method. The method comprises: providing a pharmaceutical composition which comprises a therapeutic agent and an MRI contrast agent, the pharmaceutical composition being in liquid form; and pressuring the pharmaceutical composition through at least one direct convective interstitial infusion catheter into an interstitial volume of a tissue. According to further features in preferred embodiments of the invention described below, the method further comprises imaging a region containing the tissue by magnetic resonance imaging (MRI) thereby providing at least one magnetic resonance (MR) image of the region.

According to still an additional aspect of the present invention there is provided a method of preparing a pharmaceutical composition for direct convective interstitial infusion, the method comprises co-formulating a therapeutic agent and an MRI contrast agent.

According to a further aspect of the present invention there is provided a pharmaceutical composition which comprises a therapeutic agent and an MRI contrast agent. According to further features in preferred embodiments of the invention described below, the pharmaceutical composition is in a liquid form.

According to further features in preferred embodiments of the invention described below, the MRI contrast agent is selected so as to allow convection of the MRI contrast agent together with the therapeutic agent, while prolonging a time in which the MRI contrast agent remains in the tissue.

According to still further features in the described preferred embodiments the pharmaceutical agent comprises a therapeutic agent. According to still further features in the described preferred embodiments the pharmaceutical agent comprises a diagnostic agent.

According to still further features in the described preferred embodiments the MR images are selected from the group consisting of T1-weighted MR images, gradient echo MR images, diffusion-weighted MR images and T2-weighted MR images.

According to still further features in the described preferred embodiments the method further comprises dissolving or dispersing an MRI contrast agent in the pharmaceutical composition.

According to still further features in the described preferred embodiments the method further comprises using the images (preferably the T1-weighted MR images) for monitoring the convection of the pharmaceutical agent within the tissue.

According to still further features in the described preferred embodiments the convection monitoring comprises correlating an intensity level of the images with a level of presence of the therapeutic agent.

According to still further features in the described preferred embodiments the convection monitoring comprises correlating an intensity level of the images with a concentration of the therapeutic agent.

According to still further features in the described preferred embodiments the convection monitoring comprises calculating distribution volume of the pharmaceutical composition.

According to still further features in the described preferred embodiments the convection monitoring comprises calculating expansion rate of the pharmaceutical composition.

According to still further features in the described preferred embodiments the convection monitoring comprises determining a direction of expansion of the pharmaceutical composition.

According to still further features in the described preferred embodiments the convection monitoring comprises detection backflow of the pharmaceutical composition along one or more of the direct convective interstitial infusion catheters. According to still further features in the described preferred embodiments the convection monitoring comprises leakage of the pharmaceutical composition into other low resistance paths, such as, but not limited to, necrotic regions or regions of liquid accumulation.

According to still further features in the described preferred embodiments the method further comprises using the images (preferably the diffusion-weighted or T2-weighted MR images) for determining a response of the tissue to the pharmaceutical agent.

According to still further features in the described preferred embodiments the response of the tissue is determined by calculating apparent diffusion coefficient (ADC) of the tissue and correlating the ADC with the response of the tissue. The response of the tissue is preferably determined by comparing baseline ADC maps, acquired prior to the treatment, to the ADC maps acquired during or subsequently to the treatment.

According to still further features in the described preferred embodiments the determining the response of the tissue comprises generating an ADC map of the tissue and of neighboring tissues.

According to still further features in the described preferred embodiments the response of the tissue comprises a cytotoxic response.

According to still further features in the described preferred embodiments the response of the tissue comprises a necrotic response.

According to still further features in the described preferred embodiments the response of the tissue comprises an inflammatory response. Imaging of non-specific cytotoxic tissue response can also be used for reformulating the composition so as to obtain a composition with minimal non-specific toxicity.

According to still further features in the described preferred embodiments the MRI contrast agent comprises a paramagnetic metal.

According to still further features in the described preferred embodiments the MRI contrast agent comprises a superparamagnetic metal.

According to still further features in the described preferred embodiments the MRI contrast agent comprises a ferromagnetic paramagnetic metal.

According to still further features in the described preferred embodiments the MRI contrast agent has a T1 shortening effect.

According to still further features in the described preferred embodiments the MRI contrast agent has a T2 shortening effect.

According to still further features in the described preferred embodiments the MRI contrast agent comprises a diethylenetriamine pentaacetic acid (DTPA).

According to still further features in the described preferred embodiments the paramagnetic metal comprises Gadolinium (Gd).

According to still further features in the described preferred embodiments the MRI contrast agent comprises Gadolinium-diethylenetriamine pentaacetic acid (Gd-DTPA).

According to still further features in the described preferred embodiments the tissue is a tumor.

According to still further features in the described preferred embodiments the tissue is a tumor, a brain pathology, a spine pathology, a prostate pathology, a kidney pathology, a liver pathology or any other pathology in other body organs.

The present invention successfully addresses the shortcomings of the presently known configurations by providing methods and compositions enjoying properties far exceeding the prior art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a flowchart diagram of a method suitable for administering a pharmaceutical agent to a tissue by direct convective interstitial infusion, according to various exemplary embodiments of the invention;

FIG. 2A is a flowchart diagram of a method suitable for preparing a pharmaceutical composition for direct convective interstitial infusion, according to various exemplary embodiments of the invention;

FIG. 2B is a flowchart diagram of a method suitable for preparing a pharmaceutical composition with minimal non-specific toxicity for direct convective interstitial infusion, according to various exemplary embodiments of the invention;

Figure 6:
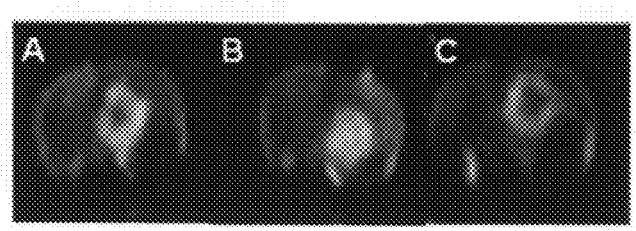
Figure 7:
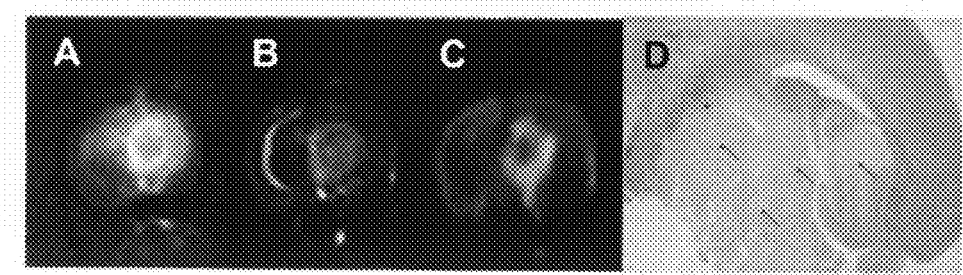

FIGS. 3A-B are T1 and T2-weighted axial MR images of normal rat brain;

FIGS. 3C-E are T1-weighted MR images acquired immediately post CED treatment with infusates containing Gd-DTPA and Evans Blue, showing poor (FIG. 3C), moderate (Figure D) and efficient (Figure E) convective efficiency;

FIGS. 3F-H show fixated brain samples of the same rats of FIGS. 3C-E, demonstrating similar distributions of the Evans Blue dye in the tissue;

FIGS. 4A-B are axial T1-weighted MR images acquired immediately post infusion of 5% (FIG. 4A) and 20% (FIG. 4A) sucrose solutions, according to various exemplary embodiments of the invention;

FIG. 5 shows convection efficacy as a function of relative viscosity;

FIGS. 6A-C are diffusion-weighted MR images of rats treated with Taxol® (FIG. 6A), Cremophor (FIG. 6B) and Carboplatin (FIG. 6C);

FIG. 7A is a T1-weighted MR image, acquired immediately following CED of Taxol® mixed with Gd-DTPA;

FIGS. 7B-C are T2-weighted (FIG. 7B) and diffusion-weighted (FIG. 7C) MR images of the same rat as FIG. 7A acquired 24 hours later;

FIG. 7D is a low-power magnification of an en block-resected lesion taken from the rat brain of FIGS. 7A-C.

Figure 1:
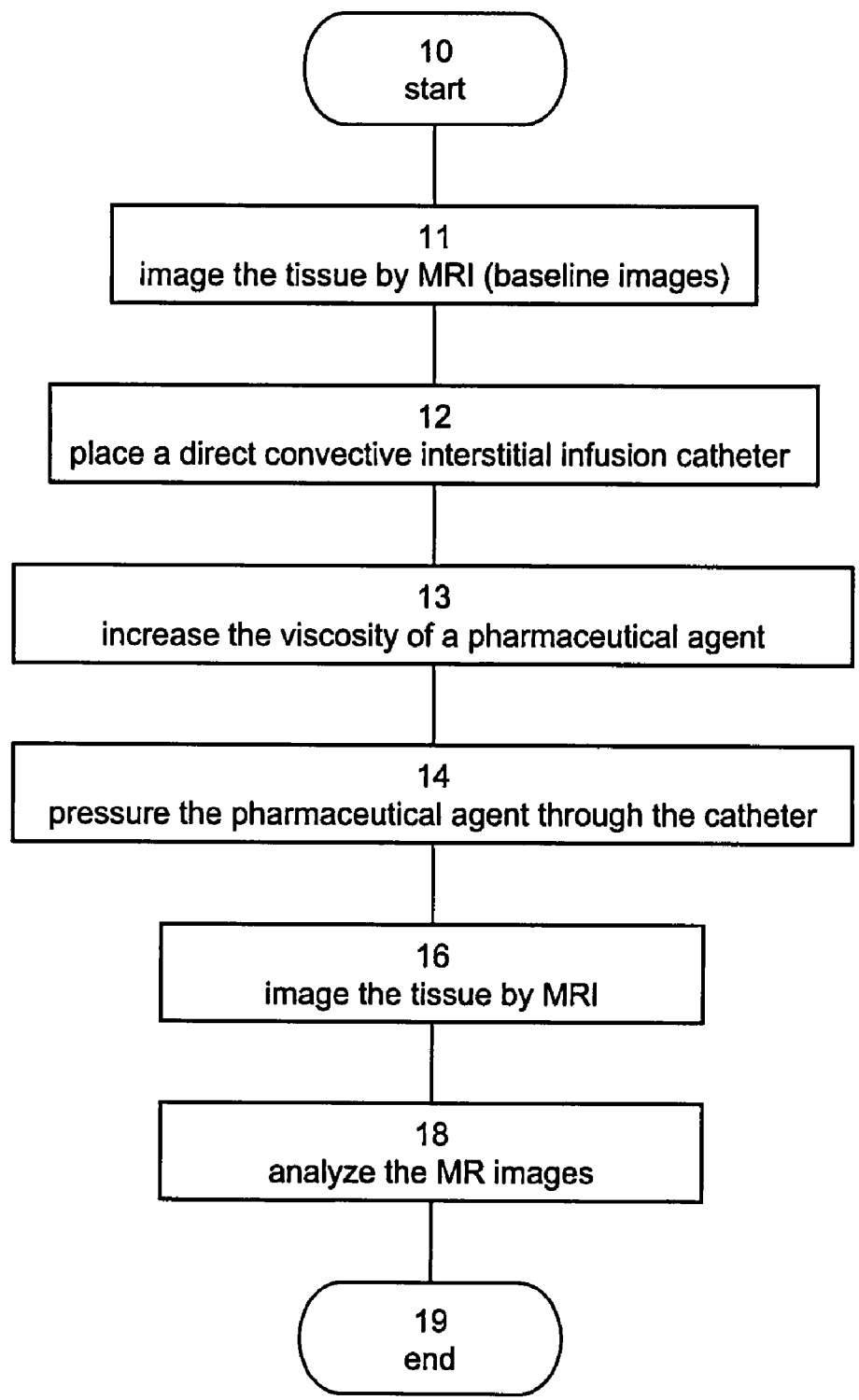
Figure 2A:
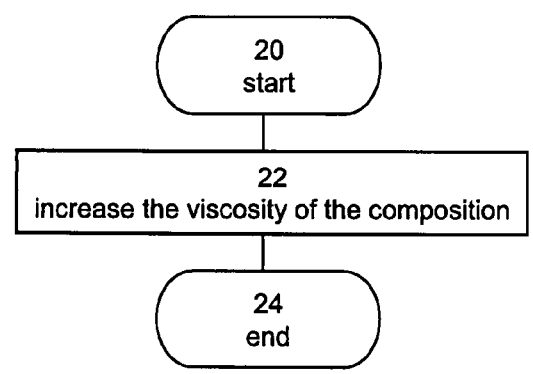
Figure 2B:
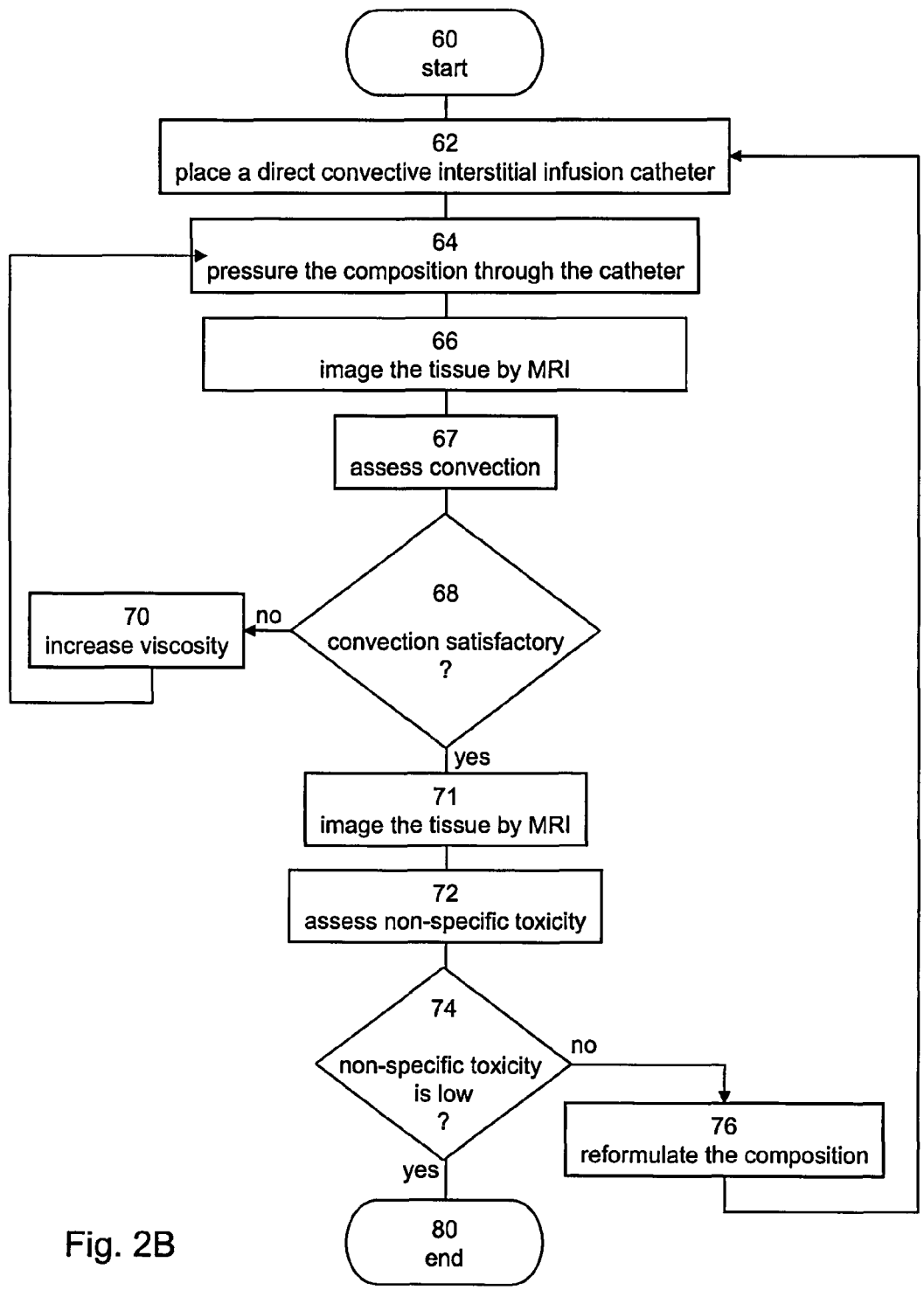
Figure 3:
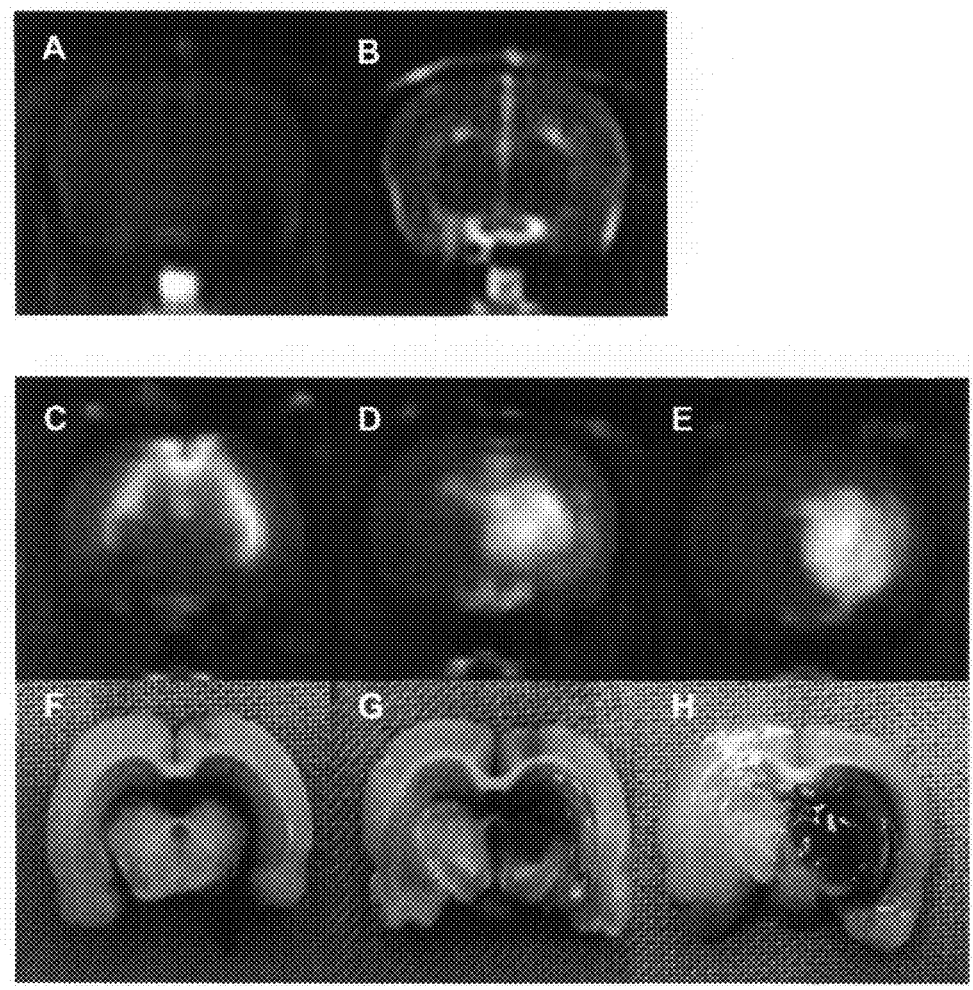
Figure 8:
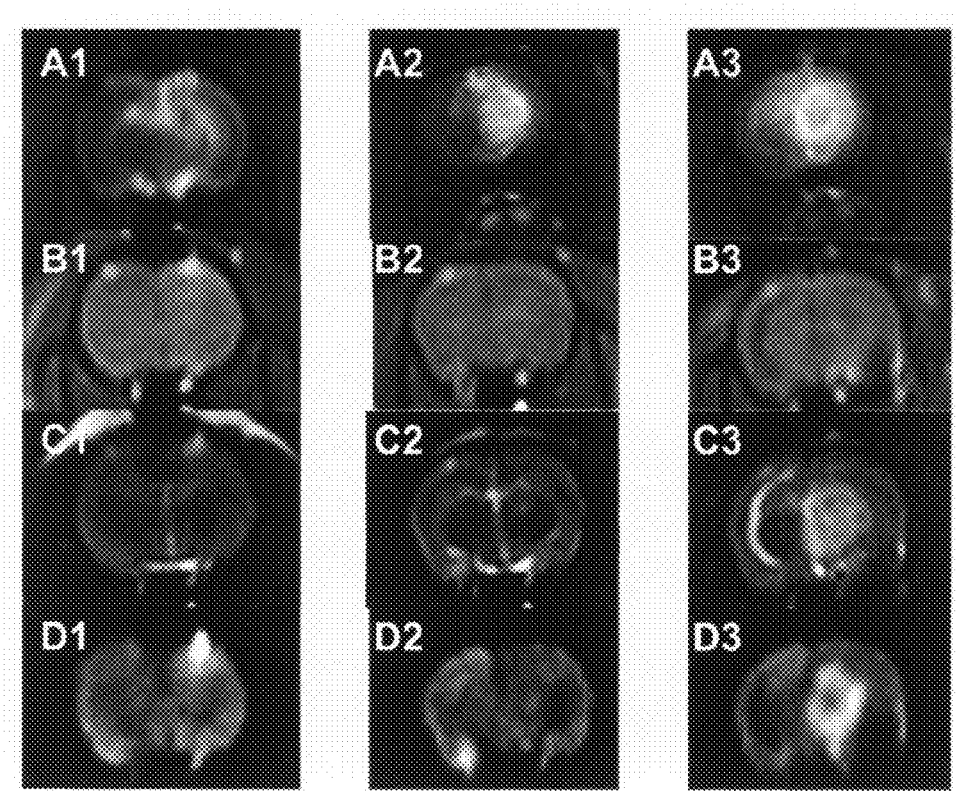
Figure 10A:
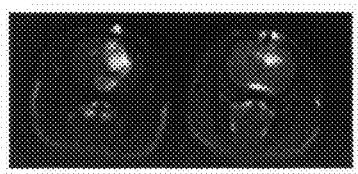
Figure 10B:
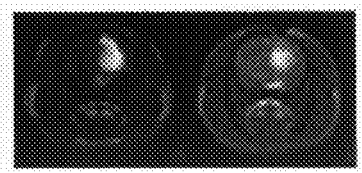
Figure 10C:
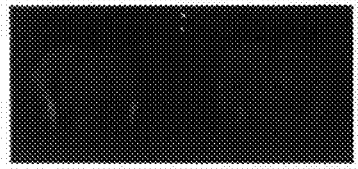
Figure 10D:
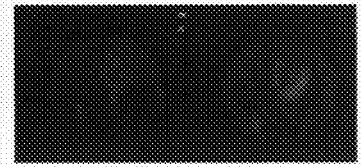
Figure 10E:
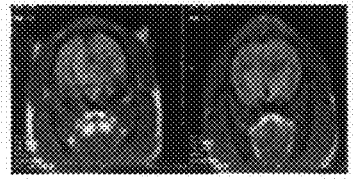
Figure 10F:
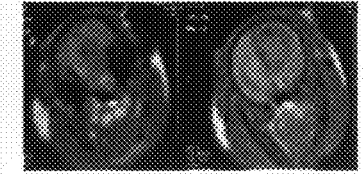
Figure 11A:
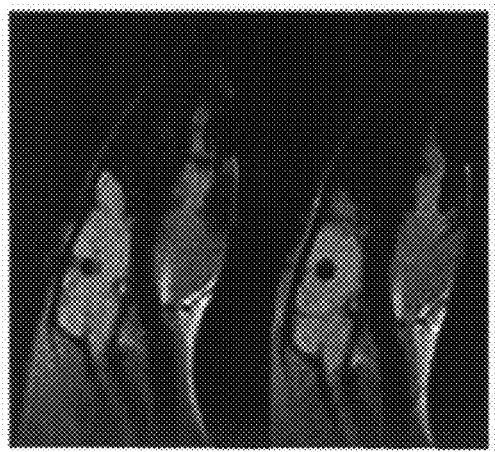
Figure 11B:
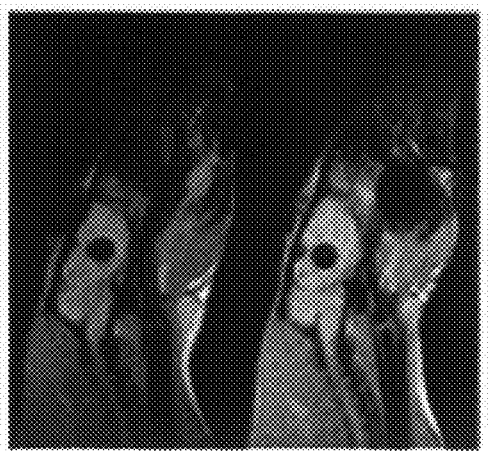
Figure 15A:
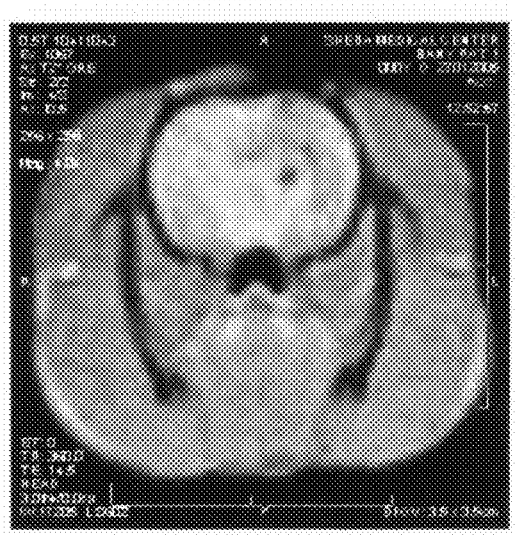
Figure 15B:
Figure 15C:
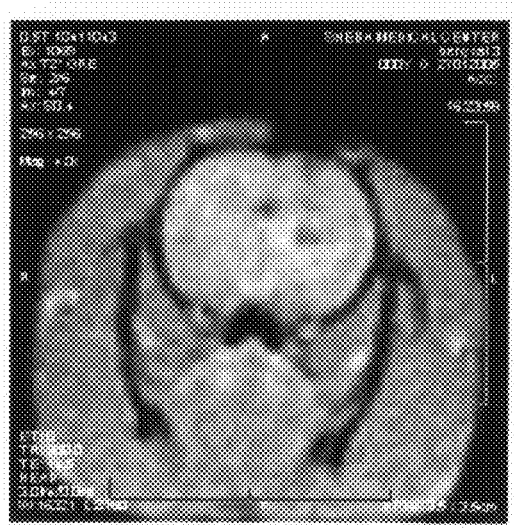
Figure 16A:
Figure 16B:
Figure 16C:
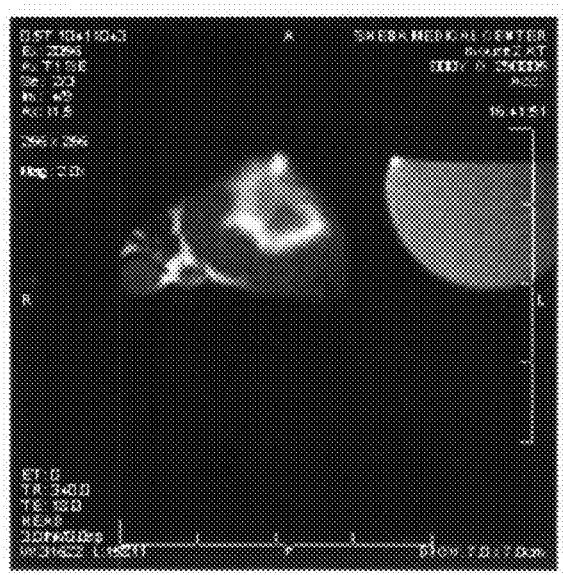
Figure 16D:
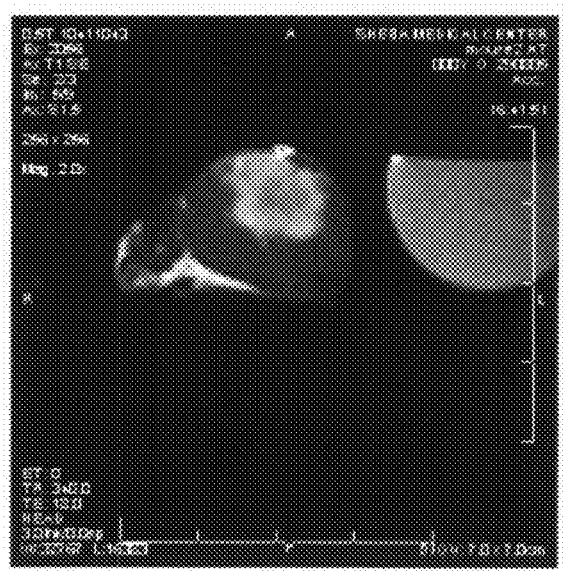
Figure 16E:
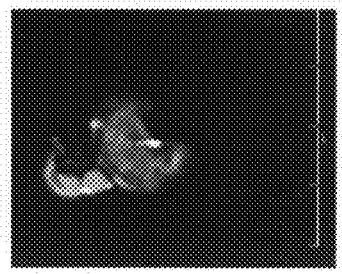
Figure 16F:
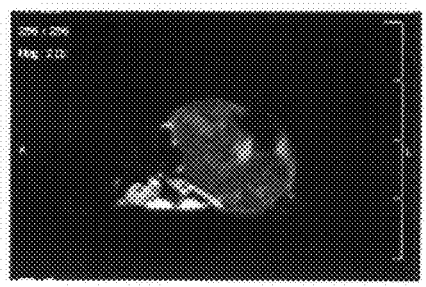
Figure 16G:
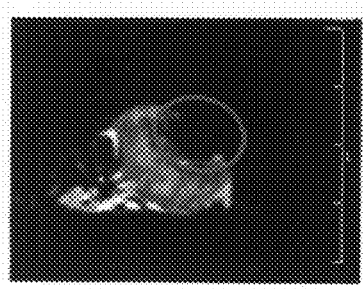
Figure 16H:
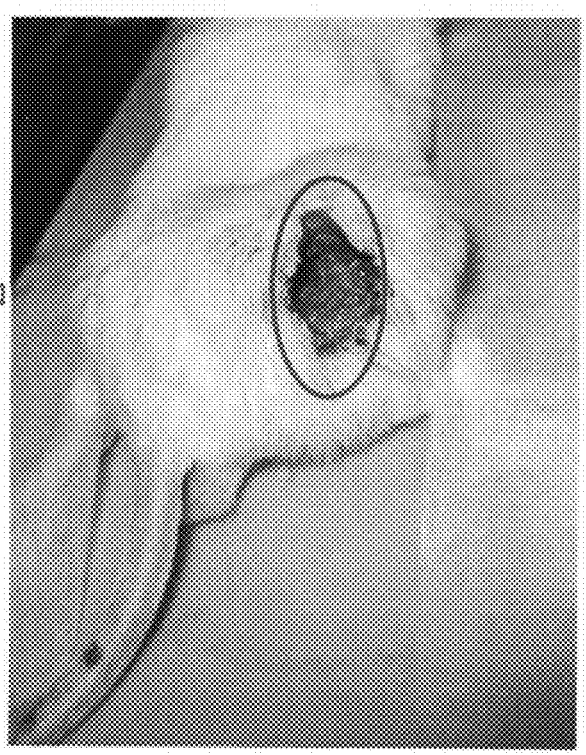
Figure 17A:
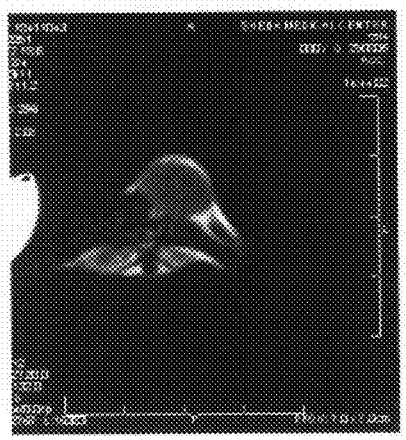
Figure 17B:
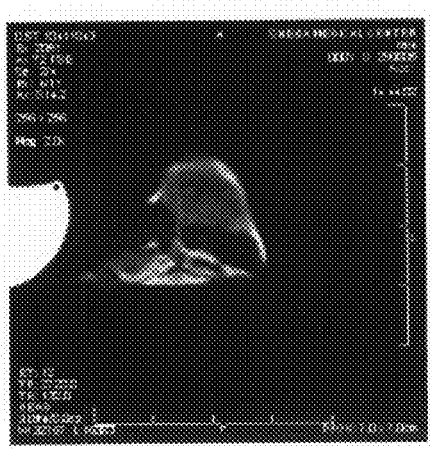
Figure 17C:
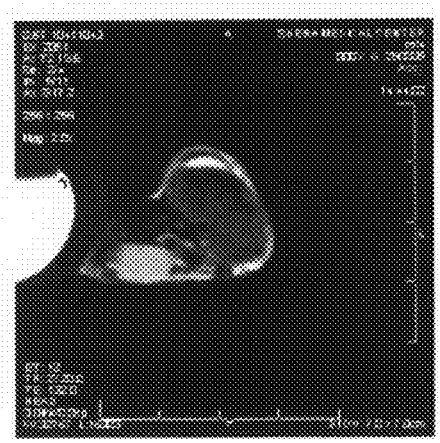
Figure 17D:
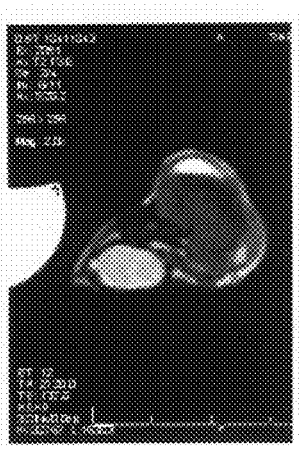
Figure 17E:
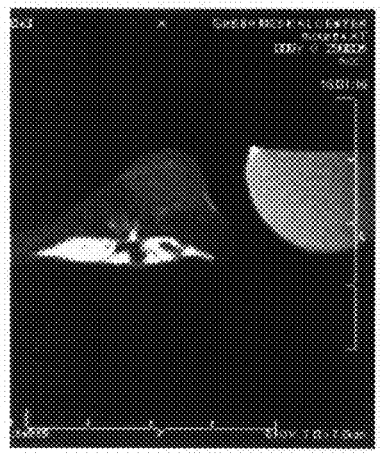
Figure 17F:
Figure 17G:
Figure 17H:
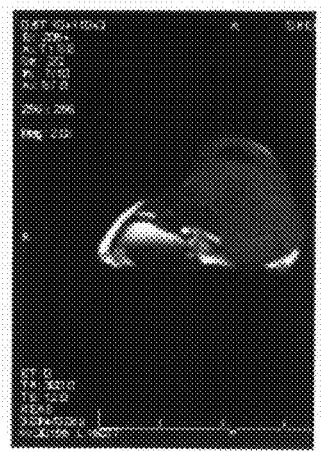
Figure 17I:
Figure 17J:
Figure 17K:
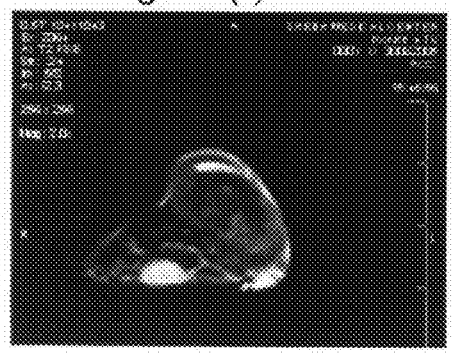
Figure 17L:
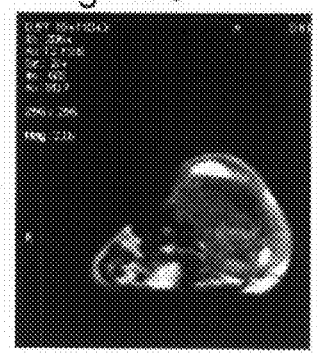
Figure 17M:
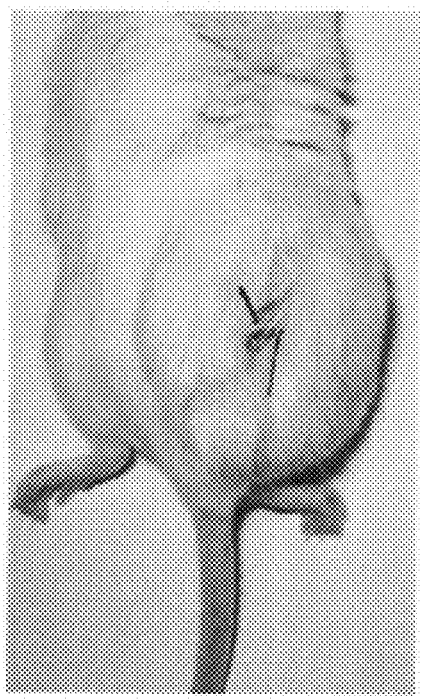
Figure 18A:
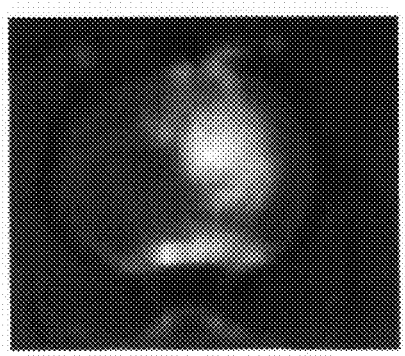
Figure 18B:
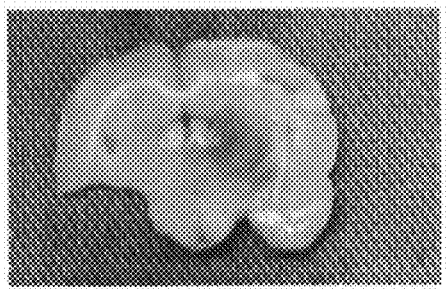
Figure 19A:
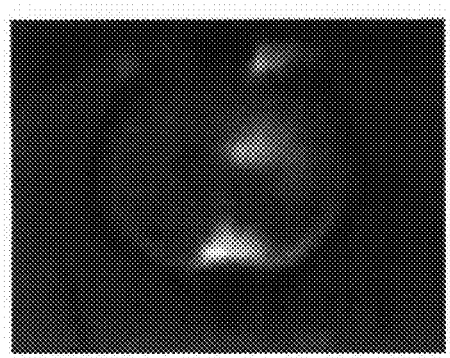
Figure 19B:
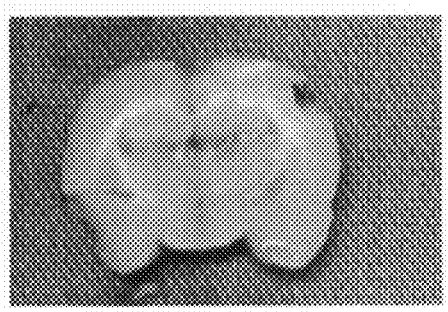
Figure 20A:
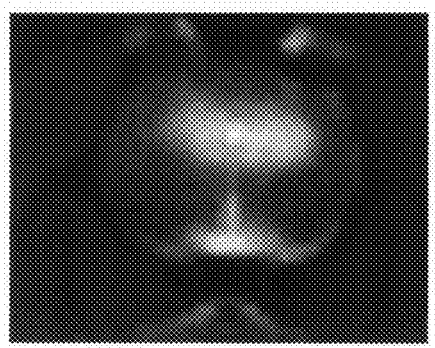
Figure 20B:
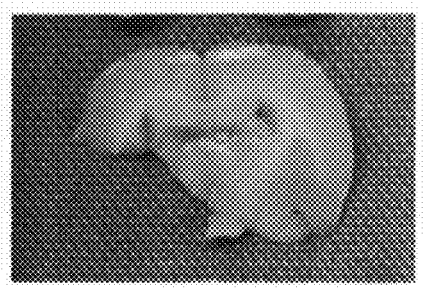
Figure 21A:
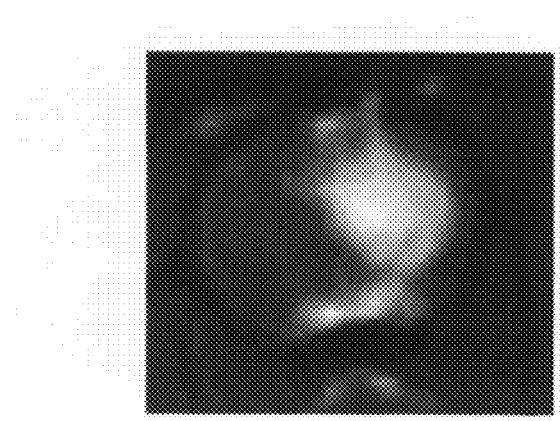
Figure 21B:
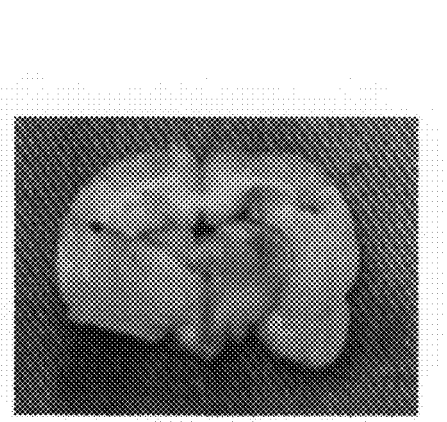
Figure 22A:
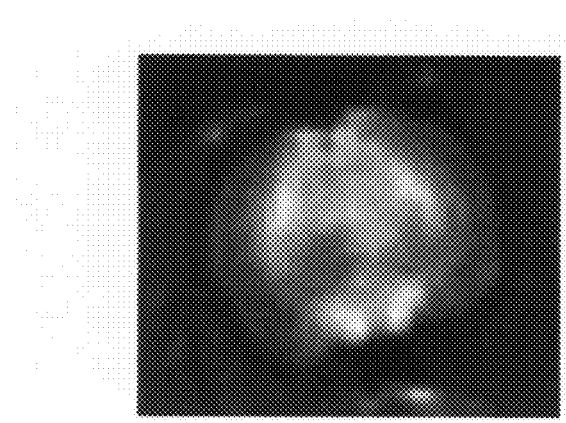
Figure 22B:
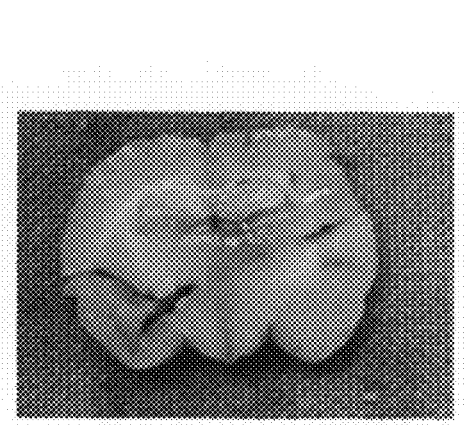

FIGS. 8A1-A3 are T1-weighted MR images acquired immediately post treatment with Gd-DTPA mixed with: 0.2% human serum albumin (FIG. 8A1), 17% sucrose (FIG. 8A2) and Taxol (FIG. 8A3);

FIGS. 8B1-B3 are T1-weighted MR images acquired 24 hours post treatment with Gd-DTPA mixed with: 0.2% human serum albumin (FIG. 8B1), 17% sucrose (FIG. 8B2) and Taxol (FIG. 8B3);

FIGS. 8C1-C3 are T2-weighted MR images acquired 24 hours post treatment with Gd-DTPA mixed with: 0.2% human serum albumin (FIG. 8C1), 17% sucrose (FIG. 8C2) and Taxol (FIG. 8C3);

FIGS. 8D1-D3 are diffusion-weighted MR acquired 24 hours post treatment with Gd-DTPA mixed with: 0.2% human serum albumin (FIG. 8D1), 17% sucrose (FIG. 8D2) and Taxol (FIG. 8D3);

FIGS. 9A-C show correlation between enhancement volume in T1-weighted MRI and enhancement volume in diffusion-weighted MRI;

FIG. 10A is a T1-weighted MR image acquired immediately post treatment in accordance with preferred embodiments of the present invention with Carboplatin (4 mg/ml);

FIG. 10B is a T1-weighted MR acquired immediately post treatment in accordance with preferred embodiments of the present invention with Carboplatin and 12% sucrose;

FIG. 10C is a diffusion-weighted MR image acquired 24 hours post treatment in accordance with preferred embodiments of the present invention with Carboplatin (4 mg/ml);

FIG. 10D is a diffusion-weighted MR image acquired 24 hours post treatment in accordance with preferred embodiments of the present invention with Carboplatin and 12% sucrose;

FIG. 10E is a T1-weighted MR image acquired 4 days post treatment in accordance with preferred embodiments of the present invention with Carboplatin (4 mg/ml);

FIG. 10F is a T1-weighted MR image acquired 4 days post treatment in accordance with preferred embodiments of the present invention with Carboplatin and 12% sucrose;

FIGS. 11A-B are gradient echo MR images acquired immediately post treatment with low viscosity (FIG. 11A) and high viscosity (FIG. 11B) of infusate containing iron oxide nanoparticles, in accordance with preferred embodiments of the present invention;

FIGS. 12A-D show: backflow into the ventricles as depicted by gradient-echo MRI immediately post a CED treatment with a 0.2 mg/ml infusate at 8 µl/min over 7.5 min (FIG. 12A); efficient IO distribution as depicted by gradient-echo MRI immediately post a CED treatment with a 0.2 mg/ml infusate at 4 µl/min over 15 min (FIG. 12B); efficient IO distribution as depicted by direct visualization immediately post treatment with a high concentration infusate (FIG. 12C); and efficient fluorescent-labeled IO distribution as depicted by spectral imaging immediately post treatment, FIGS. 13A-D show gradient-echo MR images of a rat taken immediately (FIG. 13A), 3 days (FIG. 13B), 6 days (FIG. 13C) and 27 days (FIG. 13D) post a CED treatment with a 0.2 mg/ml infusate at 4 µl/min over 15 minutes;

FIGS. 14A-D show gradient-echo MR images of another rat, taken immediately (FIG. 14A), 3 days (FIG. 14B), 6 days (FIG. 14C) and 27 days (FIG. 14D) post a CED treatment with a 0.2 mg/ml infusate at 4 µl/min over 15 minutes;

FIGS. 15A-C show gradient-echo MR images of three rats taken immediately post treatment with low concentration IO in 20% sucrose solution at infusion rates of 1 µl/min over 30 minutes (FIGS. 15A-B), and 2 µl/min over 15 minutes (FIG. 15D);

FIGS. 16A-H show an example of a large C26 tumor induced in the thigh of a balb-c mouse treated by CED of high concentration (thus high viscosity) Paclitaxel, where FIGS. 16A-B are T2 MR images of the tumor prior to treatment, FIGS. 16C-D are T1 MR images taken immediately post treatment, FIGS. 16E-G are T2 MR images taken 24 hours post treatment, and FIG. 16H is an image of the treated mouse;

FIGS. 17A-M show an example of a large C26 tumor induced in the thigh of another balb-c mouse treated by CED of high concentration Paclitaxel, where FIGS. 17A-D are T2 MR images of the tumor prior to treatment, FIG. 17E-H are T1 MR images taken immediately post treatment, FIG. 17(I)-L are T2 MR images taken 24 hours post treatment, and FIG. 17M is an image of the treated mouse; and FIGS. 18A-22B are T1-weighted MR images (A) and respective optical images (B) of brains of five different rats, treated by CED with high viscosity infusates containing blue bovine serum albumin and Gd-DTPA.

FIGS. 23A-H are MR images acquired immediately (FIGS. 23A-D) and 24 hours (FIGS. 23E-H) post treatment in non-specific neurotoxicity experiments where different solvents were used for dissolving Taxol.

DESCRIPTION OF THE PREFERRED EMBODIMENTS

The present embodiments are of pharmaceutical compositions which can be used in drug delivery. Specifically, the present embodiments can be used to improve the efficiency of direct convective interstitial infusion. The present embodiments are further of methods for (i) formulating the pharmaceutical compositions, (ii) preparing the pharmaceutical compositions for direct convective interstitial infusion and (iii) administering the pharmaceutical compositions to a tissue or tissues.

The principles and operation of compositions and methods according to the present embodiments may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In a search for improving the efficiency of direct convective interstitial infusion, the present inventors have uncovered that using a composition having sufficiently high values of viscosity, significantly improves infusion of the composition into interstitial volumes of the tissue, while minimizing backflow.

Hence, according to one aspect of the present invention there is provided a pharmaceutical composition which comprises a pharmaceutical agent and a pharmaceutical carrier.

As used herein, "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutical carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Representative examples of excipients include, without limitation, calcium carbonate, calcium phosphate, various sugars and types of starch, cellulose derivatives, gelatin, vegetable oils and polyethylene glycols.

The composition of the present embodiments is preferably in a liquid form, which can be, a solution, a suspension, an emulsion and the like. Thus, for example, in one embodiment, the pharmaceutical carrier is in a liquid form and the pharmaceutical agent is dissolved or dispersed in the pharmaceutical carrier. In another embodiment, the pharmaceutical agent is in a liquid form and is co-formulated (e.g., mixed) with the pharmaceutical carrier.

In various exemplary embodiments of the invention the pharmaceutical composition has a sufficiently high viscosity.

As used herein "sufficiently high viscosity" refers to a viscosity value such that during direct convective interstitial infusion using a properly placed catheter(s), a perfusion of the composition into interstitial volumes of a tissue is ensured with minimal or substantially without backflow.

The viscosity is conveniently expressed in relative value, in units of saline viscosity or the like. As demonstrated in the Examples section that follows (see Table 1 and FIG. 5) it was found by the Inventors of the present invention that CED efficiency (for example, in terms of CED volume) is an increasing function of the viscosity of the composition. Specifically it was found that efficient CED can be obtained when the viscosity is higher than the viscosity of a human serum albumin (HSA) solution at a concentration of about 0.2%. It was also found by the inventors of the present invention that efficient CED can be obtained when the viscosity is higher than the viscosity of sucrose 5%.

As used herein the term "about" refers to +10%.

Thus, in various exemplary embodiments of the invention the viscosity is above a predetermined viscosity value, which equals the viscosity of 0.2% HSA, more preferably, more preferably the viscosity of 1.2% HSA, more preferably the viscosity of 2% HSA, more preferably the viscosity of 3% HSA, more preferably the viscosity of 4% HSA, more preferably the viscosity of 5% HSA. When compared to the viscosity of sucrose, the viscosity is above a predetermined viscosity value, which preferably equals the viscosity of sucrose 5%.

Before providing a further detailed description of the composition as delineated hereinabove and in accordance with various exemplary embodiments of the present invention, attention will be given to the advantages offered thereby.

It is recognized that a major limitation of prior art liquids used in CED, is that too high flow rate or pressure in the interstitial infusion catheter results in backflow of the liquid along an outer wall of the catheter. At high flow rate or pressure, the resistance of the tissue to the liquid flow forces the prior art liquids to bypass the interstitial volumes and enter other small nearby gaps, such as the gap formed along the catheter's path. This bypass or backflow is known to causes non-specific toxicity by high drug levels in the cerebrospinal fluid.

In contrast, due to the sufficiently high viscosity, the composition of the present embodiments is constrained to generally flow in a direction dictated by the catheter. The viscosity is a manifestation of significant intermolecular friction forces present in the composition. Due to these friction forces large diversions from the original flow direction are energetically less favored and the backflow is substantially prevented or at least minimized. According to a preferred embodiment of the present invention the viscosity of the composition allows pressuring of the composition at higher flow rates, while minimizing backflow.

Due to its high viscosity, agents present in the composition of the present embodiments can remain in the tissue for a prolong period of time (slow washout), thus enabling slow drug release.

The high viscosity of the composition of the present embodiments also allows better control over the distribution of the composition. As will be appreciated by one ordinarily skilled in the art, the higher viscosity of the composition compared to prior art liquids, makes the composition of the present embodiments less susceptible to low resistance paths in the tissue. According to a preferred embodiment of the present invention the viscosity of the composition is selected so as to allow a substantially spherical distribution of the composition near the catheter tip. Such control over the distribution of the composition can be advantageously used for optimizing the treatment. In particular, knowing the expected distribution of the composition near the catheter tip enable a more accurate planning of the number of catheters and their position.

As will be appreciated by one ordinarily skilled in the art, the substantially spherical distribution of the composition of the present embodiments near the catheter to tip enables better planning of catheter positioning and a more accurate pre-treatment estimate of treatment extent. Additionally, the reduced backflow along the catheter path reduces nonspecific toxicity caused by high concentrations of the composition along the catheter path and in the cerebrospinal fluid (CSF). An additional advantage of the composition of the present embodiments is that wound healing complications at the catheter entry point can be avoided. The reduced backflow also facilitates faster drug distribution over larger volumes thereby enabling shorter treatment periods.

As the high viscosity of the composition of the present embodiments improves the CED efficacy, the composition can comprise large molecules and/or particles. CED of large particles enables slow release and/or targeted drug delivery, since large particles may be designed for slow release of drugs and/or can be targeted to specific sites, tissue types, cells etc.

In various exemplary embodiments of the invention the viscosity of the composition is selected to allow a flow rate of above 4 microliters per minute, more preferably 5 microliters per minute, more preferably 8 microliters per minute, more preferably 10 microliters per minute.

The ability to use high flow rates and pressure is advantageous for more than one reason. First, with high flow rates and pressure higher doses of pharmaceutical agents can be delivered within shorter treatment durations. Second, due to the synergistic nature of increased pressure and drug effect, the high flow rates and pressure enhance the therapeutic efficiency of the pharmaceutical agent.

Another advantage of using a composition with high viscosity is the ability of the composition of the present invention to overcome the tissue resistance to convection. Thus, unlike the prior art low viscosity liquids which bypass high resistance regions and flow with the cerebrospinal fluid, the composition of the present embodiments efficiently penetrates into the interstitial volumes of the tissue even in regions of high resistance to convection, such as, but not limited to, high pressure tumoral tissue, fybrotic tissue and the like. Furthermore, the composition of the present embodiments facilitate convection expansion in the interstitial zone, while allowing drugs present in the composition to penetrate into the cells.

An additional advantage of the present embodiments is the ability of the composition to remain in the interstitial volumes for a prolonged period of time as compared to the prior art. The significant intermolecular friction forces present in the composition of the present embodiments restrict the composition from escaping the interstitial volumes. Additionally, the increased viscosity of the composition significantly reduces drug degradation (for example due to slower exposure of the pharmaceutical agent to the central nervous system enzymes).

When the pharmaceutical agent contains therapeutic agent, longer periods of time in which the agent is present in the interstitial volumes improve the treatment efficiency. This facilitates the optimization of drug and dose design. Thus, for example, the use of the composition of the present embodiment allows lower drug concentration and lower treatment duration, while maintaining efficient therapeutic effect with minimal or no side effects. In addition, longer prescience of the therapeutic agent enhances presentation of tumor antigens to the immune system and provokes more efficient immune response.

When the pharmaceutical agent contains a diagnostic agent (e.g., an MRI contrast agent, a radioactive agent, etc.), longer periods of time in which the agent is present in the interstitial volumes improve the diagnostic efficiency.

Another advantage of the composition of the present invention is that the high viscosity allows the use of agents which, to date, were not suitable to be used in convective based infusion, for example, due to damage caused to these agents during the application of pressure. A representative example of such an agent is a gene therapy agent or a gene-related therapy related agent, e.g., RNA, anti-sense and the like. Additionally, the high viscosity of the composition of the present embodiments allows the use of therapeutic and/or diagnostic agents with high (e.g., above 200 kDa) molecular weight. The high viscosity also allows the administration by CED of nanoparticles, including, without limitation, iron oxide nanoparticles.

The significant improved convection efficiency makes the composition of the present invention suitable to be used in CED treatments of tumors or other pathologies in the central nervous system as well as other body organs, such as, but not limited to, the prostate, pancreas, kidney and the liver.

Pharmaceutical compositions of the present embodiments may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present embodiments thus may be formulated in conventional manner using one or more physiologically acceptable carriers comprising excipients and auxiliaries, which facilitate processing of the active ingredients into preparations that can be used pharmaceutically.

The active ingredients of the pharmaceutical composition may be formulated in aqueous solutions, preferably in physiologically compatible buffers such as Hank's solution, Ringer's solution or physiological salt buffer.

Pharmaceutical carriers which can increase the viscosity include, without limitation, serum albumin, sucrose and methanol. Additionally, when the pharmaceutical composition is in a suspension form, substances that increase the viscosity of the suspension may be used. Such substances include, without limitation, sodium carboxymethyl cellulose, sorbitol, or dextran. Optionally, the suspension may also contain suitable stabilizers or agents that increase the solubility of the active ingredients, to allow for the preparation of highly concentrated solutions.

Viscosity may also be increased by binding to the therapeutic agent molecules which significantly increase water adhesion such as Dextrane or Albumin.

The pharmaceutical compositions of the present embodiments can comprise a therapeutic agent and/or a diagnostic agent. The composition of the present embodiments can also include stem cells, in which case the composition can be used for high dose stem cell transplantation. The high viscosity composition may also protect the stem cells (which are sensitive to the pressure) during the delivery into the target tissue.

Therapeutic agents include active ingredients which are contained in the pharmaceutical composition is an amount effective to achieve the intended purpose. More specifically, a "therapeutically effective amount" means an amount of active ingredients (e.g., an anti-proliferative agent, a chemotherapeutic agent, a nucleic acid construct) effective to prevent, alleviate, or ameliorate symptoms of a disorder or prolong the survival of the subject being treated. Determination of a therapeutically effective amount is well within the capability of those skilled in the art, especially in light of the detailed disclosure provided herein.

Many therapeutic agents are contemplated. Representative examples include, without limitation, chemotherapeutic agents (e.g., neurooncologic agents), anti-inflammatory agents (steroidal and non-steroidal), gene therapy agents, antipruritic agents, anesthetic agents, antimicrobial agents, anti-oxidants, antidepressants, vitamins, antihistamines, hormones, androgenic compounds, progestin compounds and drug carriers for slow drug release or targeting.

Examples of chemotherapeutic or chemotherapeutic-related agents include, without limitation, Cremophor, Taxol®, Carboplatin and Ethanol.

Nevertheless, it was found by the Inventors of the present invention that when the composition is used for treating brain tumors, the presence of Cremophor in the composition results in non specific toxic response. Thus, in situations in which Cremophor may result in non specific toxic response (e.g., in brain tumor treatments), the pharmaceutical composition is preferably Cremophor free. Additional examples of chemotherapeutic agents include, without limitation, an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant. Other examples include, without limitation, BCNU (Carmustine); Irinotecan (CPT-11); Camptothecin (CPT); toptecan; Oxaliplatin; Carboplatin; Cisplatin (CDDP); CCNU (Lomustine); Doxorubicin; 5' Fluoro uracil (5FU); Methotrexate; Vinblastine; Vincristine; AS101, Procarbazine (Matulane); etoposide (VP-16); Gemzar (Gemcytabine . . . for pancreas, etc); Doxil; Navelbine; Cytarabine-A; (Depo-Cyt (in liposomal form); Herceptin, Raloxifene, Tamoxifen, Meace (anti-Progesterone); Somatastati (pituitary); 1-131 (radioactive iodine for thyroid); IL-2, IL12 (melanoma, renal), cytoxan, cyclophosphamide, TS-1, CDDP, rosiglitazone, metformin.

Also contemplated are Taxol®, formulations, such as, but not limited to, ABI-007; CT-2103 (PG-TXL); Fibrinogen-Coated Emulsion Formulation of Docetaxel; Genetaxyl; Liposome-encapsulated paclitaxel (LEP); OncoGel; Paclimer Microspheres; PacoExtra; Paxoral; PEG-paclitaxel; S-8184; SP5.210C; Taxoprexin; Taxosomes/Dermos; Xyotax; Taxoprexin; RPR109881; Ixabepilone; Abraxane.

Examples of neurooncologic agents include, without limitation, Antineoplaston A10, Antineoplaston AS2-1, Batabulin (T67), Gimatecan, INO 1001 (Pardex), Irofulven, Ixabepilone, CC 8490, Celgene; TP38, Cilengitide; Enzastaurin; Erlotinib (tarceva); Gefitinib (iressa); Vatalanib; AP 12009; Efaproxiral (efaproxyn); Motexafin-Gd (xyctrin); Temozolomide.

Examples of suitable non-steroidal anti-inflammatory agents include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

Examples of suitable steroidal anti-inflammatory agents include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Examples of suitable antipruritic agents include, without limitation, methdilazine and trimeprazine.

Examples of suitable anesthetic agents include, without limitation, lidocaine, bupivacaine, chlorprocaine, dibucaine, etidocaine, mepivacaine, tetracaine, dyclonine, hexylcaine, procaine, cocaine, ketamine, pramoxine and phenol.

Examples of suitable antimicrobial agents, including antibacterial, antifungal, antiprotozoal and antiviral agents, include, without limitation, beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, farnesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate and clotrimazole and mixtures thereof.

Examples of suitable anti-oxidants include, without limitation, ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethyl-chroman-2-carboxylic acid (commercially available under the trade name Trolox$^R$), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Examples of suitable antidepressants include, without limitation, norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs"), corticotropin-releasing factor (CRF) antagonists, α-adrenoreceptor antagonists, NK1-receptor antagonists, 5-HT$_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Examples of suitable vitamins include, without limitation, vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin B$_3$ (niacinamide and its derivatives), alpha hydroxy acids (such as glycolic acid, lactic acid, tartaric acid, malic acid, citric acid, etc.) and beta hydroxy acids (such as salicylic acid and the like).

Examples of suitable antihistamines include, without limitation, chlorpheniramine, brompheniramine, dexchlorpheniramine, tripolidine, clemastine, diphenhydramine, promethazine, piperazines, piperidines, astemizole, loratadine and terfenadine.

Examples of suitable hormones, include, without limitation, androgenic compounds and progestin compounds.

Examples of suitable androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Examples of suitable progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

Also contemplated are agents which are presently used in animal as well as phase I, II and III of clinical studies for convection-based therapy of brain tumors and other brain pathologies. Representative examples include, without limitation, agents known as: IL13-PE38QQR, TP-38, IL4(38-37)-PE38 KDEL, cpIL4-PE, IL-4 cytotoxin, IL4-Pseudomonas exotoxin (NBI-3001), TransMID, Tf-CRM107, HSV-1-tk gene-bearing liposomal vector, IL-12, LSFV-IL12, SP-DT', DAB389EGF, gemcitabine, carboplatin, glucocerebrosidase, AAV2-TK, LIPO-HSV-1-tk gene transfer system, TRAIL, BD-EGF and IMC-C225 (as molecular targeting agents for boron neutron capture therapy), interleukin (IL)-1beta and interferon (IFN)-gamma, HAMLET, 6-hydroxydopamine, targeted chimera cytotoxic proteins, AraC, AAV-2, topotecan, double-stranded RNA-dependent protein kinase PKR, and AP 12009. These agents are presently in animal as well as phase I, II and III of clinical studies for convection-based therapy of brain tumors and other brain pathologies.

Optionally and preferably, the therapeutic agent comprises a gene therapy or a gene-related therapy agent. As stated, the high viscosity of the composition of the present embodiments allows the use of such agents which, to date, were not suitable to be used in convective based infusion. The gene therapy agent is typically a polynucleotide, which can be introduced into cells by any one of a variety of methods known in the art (see, e.g., Sambrook, J. and Russell, D. W. (1989, 1992, 2001), Molecular Cloning: A Laboratory Manual, Cold Springs Harbor Laboratory, New York; Ausubel, R. M. et al., eds. (1994, 1989). Current Protocols in Molecular Biology, John Wiley and Sons, Baltimore, Md. (1989); Chang, P. L., ed. (1995). Somatic Gene Therapy, CRC Press, Boca Raton, Fla.; Vega, M. A. (1995). Gene Targeting, CRC Press, Boca Raton, Fla.; Rodriguez, R. L. and Denhardt, D. H. (1987). Vectors: A Survey of Molecular Cloning Vectors and Their Uses, Butterworth-Heinemann, Boston, Mass.; and Gilboa, E. et al. (1986). Transfer and expression of cloned genes using retro-viral vectors. Biotechniques 4(6), 504-512).

An advantageous approach for introducing a polynucleotide, and which is in accordance with preferred embodiments of the present invention, is by using a viral vector. Viral vectors offer several advantages, including higher efficiency of transformation and targeting to, and propagation in, specific cell types. Viral vectors can also be modified with specific receptors or ligands to alter target specificity through specific cell receptors, such as neuronal cell receptors (Kaspar, B. K. et al. 2002, Mol Ther 5, 50-56).

Retroviral vectors represent one class of vectors suitable for use with the present invention. Defective retroviruses are routinely used in transfer of genes into mammalian cells (for a review, see Miller, A. D., 1990, Blood 76, 271). Portions of the retroviral genome can be removed to render the retrovirus replication machinery defective, and the replication-deficient retrovirus can then packaged into virions, which can be used to infect target cells through the use of a helper virus while employing standard techniques. Protocols for producing recombinant retroviruses and for infecting cells with viruses in vitro or in vivo can be found in, for example, Ausubel et al., 1994, Retroviruses have been used to introduce a variety of genes into many different cell types, including neuronal cells, epithelial cells, endothelial cells, lymphocytes, myoblasts, hepatocytes and bone marrow cells.

Another suitable expression vector may be an adenovirus vector. The adenovirus is an extensively studied and routinely used gene transfer vector. Key advantages of an adenovirus vector include relatively high transduction efficiency of dividing and quiescent cells, natural tropism to a wide range of epithelial tissues, and easy production of high titers (Russel, W. C., 2000, J Gen Virol 81, 57-63). The adenovirus DNA is transported to the nucleus, but does not integrate thereinto. Thus the risk of mutagenesis with adenoviral vectors is minimized, while short-term expression is particularly suitable for treating cancer cells. Adenoviral vectors used in experimental cancer treatments are described by Seth et al., "Adenoviral vectors for cancer gene therapy," 1999, pp. 103-120, P. Seth, ed., Adenoviruses: Basic Biology to Gene Therapy, Landes, Austin, Tex.).

A suitable viral expression vector may also be a chimeric adenovirus/retrovirus vector combining retroviral and adenoviral components. Such vectors may be more efficient than traditional expression vectors for transducing tumor cells (Pan et al. 2002, Cancer Letts 184, 179-188).

A specific example of a suitable viral vector for introducing and expressing the polynucleotide sequence of the present invention in an individual is the adenovirus-derived vector Ad-TK. This vector expresses a herpes virus thymidine kinase (TK) gene for either positive or negative selection and includes an expression cassette for desired recombinant sequences. This vector may be used to infect cells that have an adenovirus receptor, which includes most cancers of epithelial origin (Sandmair et al., 2000, Hum Gene Ther 11, 2197-2205).

Features that limit expression to particular cell types can also be included on a vector construct. Such features include, for example, promoter and regulatory elements that are specific for the desired target cell type. Secretion signals generally contain a short sequence (7-20 residues) of hydrophobic amino acids. Secretion signals are widely available and are well known in the art (see, e.g., von Heijne, 1985, J Mol Biol 184, 99-105 and Lej et al., 1987, J Bacteriol 169, 4379).

Although a recombinant vector does not have to be administered locally, local administration can provide a quicker and more effective treatment. Following convective infusion, the viral vectors will circulate until they recognize host cells with appropriate target specificity for infection For any preparation used in the methods of various exemplary embodiments of the present invention, the dosage or the therapeutically effective amount of the therapeutic agents can be initially estimated from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition (see, e.g., Fingl, E. et al. (1975), "The Pharmacological Basis of Therapeutics," Ch. 1, p. 1.)

Additional therapeutic agents which can be used include neurotrophic factors (e.g., NGF, BDNF, NT-3, NT-4, NT-5, GDNF), neuroprotective factors (e.g., Eldepryl, Selegeline), endogenous angiogenic-inhibitors (e.g., 2-Methoxyestradiol, Angiostatic corticosteroids, angiostatin, endostatin, Anti-thrombin III, Arresten, Canstatin, Cartilage-derived inhibitor, CD59 complement fragment, Fibronectin fragments, Growth—related oncogene-β, Heparin hexasaccharide fragment, Heparinases, Human chorionic gonadotropin, Interferon-α/β/γ, Interferon-inducible protein, Interleukin-12, Kringle-5, Metalloproteinase inhibitors, Metallospondin, Amino-terminal fragment of platelet factor-4, Pigment epithelium—derived factor, Placental ribonuclease inhibitor, Plasminogen activator inhibitor, Platelet factor-4, Prolactin $M_r$ 16,000 fragment, Proliferin-related protein, Protamine), anti-angiogenic agents (e.g. Avastin, Topotecan, Thalidomide, CC-5013, Carboxyamidotriazole, EMD-121974, COL-3, Marimastat, Prinomastat, Pegylated-interferon α-2b, Celecoxib, LY317615), Anti-metabolites (e.g., Methotrexate, ciclesonide, DM-phencynonate hydrochloride, geranylgeranylacetone, nabumetone), Anti-angiogenic factors (e.g., endostatin, avastin), angiogenic factors of the VEGF family (e.g., VEGF-B, VEGF-C, VEGF-D, VEGF-E, $VEGF_{121}$, $VEGF_{165}$, $VEGF_{145}$), angiogenic factors of the angiopoietin family (e.g., Ang-1, Ang-2), angiogenic factors of the FGF family (e.g., aFGF, bFGF, FGF-3 to FGF-23), angiogenic factors of the PDG family (e.g., PDGF-AA, PDGF-BB, and PDGF-AB), angiogenic factors of the TGF family (e.g., TGF-α, TGF-β) or any angiogenic factor (including, without limitation EGF, TNF-α, SF, HGF, Ephrins, Integrin αVβ, Integrin β1, Interleukin-12, Interferon-α, Interferon-β, Interferon-γ, Nitric oxide, Thrombin, Midkine). Also contemplated are IVIG, IGG, FTS, ADCON-L gel, stimulated macrophages, Dihidro-beta-Agarofuran Sesquiterpenes and resinferatoxin which is known to be useful treatment of painful disorders such as trigeminal neuralgia.

The composition of the present invention can be used in treatment of many cases of neurodegenerative diseases, ischemic diseases, psychiatric conditions, intractable pain, blockers of angiogenesis, promotion of angiogenesis, inborn errors of metabolism, trauma, infectious diseases, autoimmune diseases. Representative examples include, without limitation epilepsy in which case the composition preferably comprises muscimol which a currently tested for such use, Parkinson, in which case the composition preferably comprises at least one of: muscimol, Sinemet (L-Dopa), Artane, Amantadine, GDNF, pramipexole (mirapex), ropinerole (requip), entocapone (comtan), (permax), ropinirole and mitochondrial nutrients; multiple sclerosis, in which case the composition preferably comprises at least one of: interferon, betaseron, copaxone, avonex, mitoxanthrone, requip, methotrexate and cyclophosphamide; dementia, in which case the composition preferably comprises donepezil (aricept); Alzheimer, in which case the composition preferably comprises at least one of: Namenda, flurbiprofen analogues, EGb 761, cholinesterase inhibitors, Statins, rivastigmine, donepezil, Cholinesterase inhibitors, mitochondrial nutrients, memantine, ChEI, Clioquinol, Juliflorine, *ginkgo biloba*, estrogen, nonsteroidal anti-inflammatory drugs, vitamin E, and cholinesterase inhibitors; adrenoleukodystrophy, in which case the composition preferably comprises at least one of: long-chain fatty acids, monounsaturated fatty acids, and a combination of oleic and erucic acids (also known as "Lorenzo's oil"); Stroke, in which case the composition preferably comprises at least one of: TPA, calcium channel blockers, aspirin, ticlid, dipyramidol, coumadin, rheopro, aggrenox, plavix, low molecular weight heparin, heparin, ace-inhibitors, antiplatelet agents, clopidogrel, ginsenoside Rb(1) (a ginseng saponin), CDP-choline liposomes, MMP inhibitors, AMPA Antagonist ZK 200775, MC-1, Encapsulated vascular endothelial growth factor-secreting cell grafts, Atenolol, metoprolol, paracetamol (acetaminophen) and dipyridamole; head trauma, in which case the composition preferably comprises at least one of: α-channel blockers, tricycles, clonidine, benzimidazole derivatives, Ziconotide, netilmicin, ofloxacin, erythropoietin, Thymosin-beta4, melatonin and Zinc); diseases in the prostate, in which case the composition preferably comprises at least one of: anti-hormonal agents, econazole, Silybin, silymarin, histone deacetylase inhibitor LAQ824, Rhodamine-123, docetaxel, prednisone, mitoxantrone, 2-Methoxyestradiol, Pamidronate, 1,24(S)-dihydroxyvitamin D2, OGX-011 (a 2'-methoxyethyl antisense oligonucleotide to clusterin), gefitinib, ribavirin, cyclopamine, celecoxib, SU6668 (antiangiogenic drug), inositol hexaphosphate, uracil, tegafur, Testosterone substitution, soy isoflavone genistein and amiloride; diseases in the pancreas, in which case the composition preferably comprises at least one of: Silybin, silymarin, alpha-hederin, thymoquinone, Nigella sativa, S 21403 (mitiglinide), atorvastatin (Sortis), incretins GIP and GLP-1, Sevelamer Hydrochloride, Thiazolidinediones, Nateglinide, quinone oxidoreductase (NQO1), mycophenolic acid, tacrolimus, NADPH, thioredoxin and glutaredoxin.

As stated, the pharmaceutical compositions of the present embodiments can comprise a diagnostic agent. The diagnostic agent can be combined with a pharmaceutical carrier and/or therapeutic agent, as desired. According to a preferred embodiment of the present invention the diagnostic agent is a contrast agent suitable for MRI, CT or X-ray imaging. This embodiment is particularly useful for monitoring the progress of CED.

Although, in principle, imaging can be performed without using added contrast media, in recent years many materials have been used for improving the quality of diagnostic images. In MRI, for example, materials which affect the spin re-equilibration can be used for enhancing the contrast of MR images. As further demonstrated in the Examples section that follows, the use of co-formulation of the therapeutic agent and an MRI contrast agent enables a clear visualization of the convection.

The MRI contrast agent can be either a positive or a negative MRI contract agent.

As used herein, "positive MRI contract agent" refers to an agent which increases the signal of the pharmaceutical composition relative to the nearby tissues of fluids, and "negative MRI contract agent" refers to an agent which decreases the signal of the pharmaceutical composition relative to the nearby tissues of fluids.

In any event, the MRI contrast agent is preferably selected so as to allow convection of the MRI contrast agent together with the convective wave of the therapeutic agent.

In various exemplary embodiments of the invention positive MRI contrast agents are used such that their dominant effect is to reduce the T1 relaxation time. In other exemplary embodiments of the invention negative MRI contrast agents are used such that their dominant effect is to reduce the T2 relaxation time.

In any event, as will be appreciated by one ordinarily skilled in the art, the pharmaceutical composition is distinguished from its surroundings either by an enhanced or reduced NMR signal.

The magnetic properties of the MRI contrast agent can be of any type. More specifically, the MRI contrast agent comprises a magnetic material which can be paramagnetic, superparamagnetic or ferromagnetic material.

The magnetic properties of the MRI contrast agent (and all other materials in nature) originate from the sub-atomic structure of the material. The direction as well as the magnitude of the magnetic force acting on the material when placed in a magnetic field is different for different materials. Whereas the direction of the force depends only on the internal structure of the material, the magnitude depends both on the internal structure as well as on the size (mass) of the material. Ferromagnetic materials have the largest magnetic susceptibility compared to para- or superparamagnetic materials. Superparamagnetic materials consist of individual domains of elements that have ferromagnetic properties in bulk. Their magnetic susceptibility is larger than that of the paramagnetic but smaller than that of ferromagnetic materials.

Broadly speaking, ferromagnetic and superparamagnetic MRI contrast agents are negative MRI contrast agents and paramagnetic MRI contrast agents can be either negative or positive MRI contrast agents. The effect of paramagnetic material on the magnetic resonance signal dependents on the type and concentration of the paramagnetic material, as well as on external factors, such as the strength of the applied magnetic field. In various exemplary embodiments of the invention the MRI contrast agents which comprise paramagnetic materials are positive contrast agents.

Paramagnetic materials, as used herein, refers to metal atoms or ions which are paramagnetic by virtue of one or more unpaired electrons, and excludes radioactive metal atoms or ions commonly referred to as radionuclides. Representative examples include, without limitation, the paramagnetic transition metals and lanthanides of groups 1b, 2b, 3a, 3b, 4a, 4b, 5b, 6b, 7b, and 8, more preferably those of atomic number 21-31, 39-50, 57-71, and 72-82, yet more preferably gadolinium (Gd), dysprosium (Dy), chromium (Cr), iron (Fe), and manganese (Mn), still more preferably Gd, Mn, and Fe, and most preferably Gd.

The use of Gd in convection is particularly advantageous when the composition comprises human serum albumin (HSA). It was found by the present Inventors that the use of Gd-based contrast agents significantly improves the efficiency of CED. The improved efficiency is in agreement with the known property of HSA to bind to Gd-based contrast agents [Aime et al., "New Insights for Pursuing High Relaxivity MRI Agents from Modelling the Binding Interaction of Gd(III) Chelates to HSA", Chembiochem, 2005, 6(5):818-820; Thompson et al., "Hetero-tripodal hydroxypyridonate gadolinium complexes: syntheses, relaxometric properties, water exchange dynamics, and human serum albumin binding", Inorg Chem, 2004, 43(26):8577-86; Kotek et al., "Lanthanide(III) complexes of novel mixed carboxylic-phosphorus acid derivatives of diethylenetriamine: a step towards more efficient MRI contrast agents", Chemistry, 2003, 9(23): 5899-915; McMurry et al., "The effect of a phosphodiester linking group on albumin binding, blood half-life, and relaxivity of intravascular diethylenetriaminepentaacetato aquo gadolinium(III) MRI contrast agents", J Med Chem, 2002, 45(16):3465-74; Barnhart J L and Berk R N, "Influence of paramagnetic ions and pH on proton NMR relaxation of biologic fluids", Invest Radiol, 1986, 21(2):132-6].

The MRI contrast agent preferably comprises a chelating moiety, capable of forming chelate-complexes with the paramagnetic material. These can be linear chelating moieties such as, but not limited to, polyamino polyethylene polyacetic acids [e.g., diethylenetriamine pentaacetic acid (DTPA), ethylene diamine tetraacetic acid (EDTA), triethylene tetraamine hexaacetic acid (TTHA) and tetraethylene pentaamine heptaacetic acid]; or cyclic chelating moieties such as, but not limited to, polyazamacrocyctic compounds [e.g., such as 1,4,7,10-tetra-azacyclododecane-1,4,7,10-tetraacetic acid (DOTA)].

In various exemplary embodiments of the invention the MRI contrast agent is a positive MRI contrast agent which comprises Gd-DTPA. Gd-DTPA is a positive contrast agent when observed via T1-weighted MRI and a negative contrast agent when observed via T2-weighted MRI. As T1 is more sensitive to Gd-DTPA, T1-weighted MRI is the preferred MRI technique when the contrast agent is Gd-DTPA.

Also contemplated are MRI contrast agents in a form of nanoparticles, such as, but not limited to, iron oxide nanoparticles.

The above MRI contrast agents can be co-formulated (e.g., mixed) with many therapeutic agents or solvents, include, without limitation, Cremophor, Taxol®, Carboplatin, Ethanol, sugars, human serum albumin, dimethyl sulfoxide and Dextrane. Also contemplated is any of the aforementioned agents used in animal and phase I, II and III of clinical studies.

It is expected that during the life of this patent many relevant MRI contrast agents will be developed and the scope of the term MRI contrast agents is intended to include all such new technologies a priori.

Reference is now made to FIG. 1, which is a flowchart diagram of a method suitable for administering a pharmaceutical agent to a tissue by direct convective interstitial infusion.

The method begins at step 10 and continues to step 12 in which at least one direct convective interstitial infusion catheter is placed in contact with the tissue. If the viscosity of the pharmaceutical agent is not sufficiently high, the method, optionally and preferably, continues to step 13 in which the viscosity of the pharmaceutical agent is increased, e.g., by co-formulating the pharmaceutical agent with a pharmaceutical carrier having a viscosity above the desired level or by thermal treatment (e.g., cooling the pharmaceutical composition).

The method continues to step 14 in which the pharmaceutical agent (or composition) is pressured through the catheter.

Dosage amount and administration intervals may be adjusted individually to provide sufficient plasma or brain levels of the pharmaceutical agent to induce or suppress the desired biological effect (i.e., minimally effective concentration, MEC). The MEC can be estimated from in vitro data. Dosages necessary to achieve the MEC depend on individual characteristics and route of administration. Detection assays can be used to determine plasma concentrations.

Depending on the severity and responsiveness of the condition to be treated, dosing can be of a single or a plurality of administrations, with course of treatment lasting from several minutes to several hours or days, or until cure is effected or diminution of the disease state is achieved.

The amount of pharmaceutical composition to be administered depends, of course, on the subject being treated, the severity of the affliction, the judgment of the prescribing physician and the like.

According to a preferred embodiment of the present invention the method continues to step 16 where the tissue is imaged by MRI. The imaging can be done by any MRI apparatus known in the art, and can be performed while the pharmaceutical composition is administrated, immediately after the administration and/or a predetermined period of time thereafter. The method preferably continues to step 18 in which the MR images are analyzed. Optionally and preferably, baseline MR images can be captured prior to treatment (see step 11). In this embodiment, the analysis of the MR images preferably includes a comparison of the MR images captured during or after treatment (step 16) with the baseline MR images (step 11).

The method ends at step 19.

The obtained MR images can be used for (i) monitoring the convection of the pharmaceutical composition, and/or (ii) assessing the response of the tissue (e.g., cytotoxic, necrotic, inflammatory response) to the presence of the pharmaceutical agent.

In the former case, the pharmaceutical composition preferably comprises an MRI contrast agent to allow differentiation of the pharmaceutical composition from nearby tissues or fluids. Many MRI pulse sequences can be used in the MRI for monitoring the convection. Typically, the pulse sequence is compatible with the type of MRI contrast agent present in the pharmaceutical composition.

Thus, for positive MRI contrast agents having a T1 shortening effect, the pulse sequence is preferably T1-weighted pulse sequence, and for negative MRI contrast agents, having a T2 shortening effect, the pulse sequence is preferably T2-weighted pulse sequence.

According to the presently preferred embodiment of the invention the monitoring is by comparing the images with images acquired prior to the treatment (baseline images). Additionally or alternatively, the intensity of the image or the contrast spread can be correlated with the presence of the therapeutic agent. This can be done, for example, by defining region-of-interests, and multiplying the number of pixels in the region-of-interests with the volume represented by a single pixel. As will be appreciated by one of ordinary skill in the art, such procedure can be used to define the distribution volume, expansion rate and/or direction of expansion of pharmaceutical composition. The determination of presence of the pharmaceutical composition can also be used for detecting backflow of the pharmaceutical composition along the catheter or leakage into a low resistance path such as, but not limited to, necrotic regions or regions of liquid accumulation, stopping or preventing convection formation. This information is particularly useful, for example, for the purpose of real time treatment adjustments.

The intensity level of the images can also be correlated with the concentration of the therapeutic agent in the tissue. This can be done, for example, using a predetermined functional dependence between the concentration and the intensity established prior to the treatment. Such functional dependence can be established by an appropriate set of experiments (e.g., of the type of the animal studies described in the Examples section that follows) and expressed as a lookup table, a calibration curve, an empiric mathematical expression and the like.

In the embodiment in which the MR images are used for assessing the response of the tissue to the presence of the pharmaceutical agent. The MR images are preferably diffusion-weighted MR images or T2-weighted MR images. In any event, the type of MR image of is selected so as to allow exclusive determination of the tissue response to the treatment. The imaging of the tissue can be repeated more than one time so as to monitor the response of the tissue over time. The MR images can be acquired at any time during treatment, from early stages (e.g., from a few minutes to a few hours), through later stages (e.g., several hours to a few days), to post treatment stages (from several days to several weeks).

The advantage of using diffusion-weighted MRI is that such technique allows accurate control of the diffusion direction and the time during which diffusion takes place. Additionally, diffusion-weighted MRI enables the determination of the mean diffusion path length. MRI sequences suitable for diffusion-weighted MRI are known in the art, see, e.g., Stejskal E O and Tanner J E, "Spin diffusion: Spin echoes in the presence of a time-dependent field gradient", J Chem Phys 42:288-292, 1965. As demonstrated in the Examples section that follows, the use of diffusion-weighted MRI allows exclusive detection of tissues developing cytotoxic response to the destructive treatment. Furthermore, the use of diffusion-weighted MRI allows differentiate between various response and toxicity patterns, such as, but not limited to, global, focal (typically observed as enhanced regions originating close to the catheter tip or track), cortical, gyral, diffuse, necrotic (typically characterized by high ADC) versus inflammatory (typically characterized by low ADC) and the like.

MR sequences suitable for T2-weighted MRI include fast spin-echo and other MR sequences such as, but not limited to, the MR sequences found in Friedburg H and Bockenheimer S, "Clinical NMR tomography with sequential T2 images (Carr-Purcell spin-echo sequences)" Radiologe., 1983, 23(8):353-6.

The determination of the response can be done, for example, by comparing the MR images acquired after the treatment is initiated with baseline MR images acquired prior to the treatment. When the images are diffusion-weighted MR images, an apparent diffusion coefficient (ADC) of the tissue can be calculated before and after treatment and changes in the ADC can be correlated with the response of the tissue. Still additionally, an ADC map of the tissue and neighboring tissues can be generated.

The dependence of the signal intensity of the diffusion-weighted MR images on the ADC of the tissue is given by the following exponential relation:

$$I = I_0 \exp(-b \cdot ADC), \quad (EQ. 1)$$

where I and $I_0$ are the signal intensities in the presence and absence of diffusion-weighting gradients, respectively, and b is a diffusion weighting factor, expressed in units of time per unit area. Specifically, b is given by the equation:

$$b = \gamma^2 \delta^2 g^2 (\Delta - \delta/3), \quad (EQ. 2)$$

where $\gamma$ is the gyromagnetic ratio of the nuclei, g is the strength of the diffusion-weighting gradient, $\delta$ is the duration of the diffusion-weighting gradient and $\Delta - \delta/3$ is the effective diffusion time. Knowing the value of the diffusion weighting factor, the ADC of the tissue can be calculated for any given diffusion-weighted MR image. For example, an ADC map of the tissue and neighboring tissue can be obtained by acquiring diffusion-weighted MR images at two different values of b, e.g., b=5 sec/mm² and b=1000 sec/mm².

Reference is now made to FIG. 2a, which is a flowchart diagram of a method suitable for preparing a pharmaceutical composition for direct convective interstitial infusion, according to various exemplary embodiments of the invention.

The method begins at step 20 and continues to step 22 in which the viscosity of the pharmaceutical composition is increased to a sufficient level as further detailed hereinabove. The increment of the viscosity can be done, as stated, by co-formulating the composition with a carrier having a sufficiently high viscosity or by thermal treatment (e.g., cooling the pharmaceutical composition). The method ends at step 24.

Suitable composition for the present embodiments can thus be formulated by an appropriate study plan which combines a CED procedure and magnetic resonance imaging. A representative method for preparing the composition is illustrated in the flowchart diagram of FIG. 2b.

The method begins at step 60 and continues to step 62 in which direct convective interstitial infusion catheter is placed in one or more animals. The method continues to step 64 in which a composition, mixed with an MRI agent is pressured through the catheter. The method continues to step 66 in which a region containing the tissue contacting the catheter is imaged by MRI, during or immediately post treatment.

The method continues to step 67 in which the convection extent is assessed from the MRI images. Assessment of CED formation and extent can then be performed, for example, by obtaining T1-weighted MR images immediately post treatment, and calculating the distribution volume of the composition. The calculation can be performed by defining regions-of-interests over the entire enhanced region of the images, and multiplying the number of pixels in the regions-of-interests by the volume which corresponds to a single pixel.

The method then proceeds to decision step 68 in which the methods determines whether or not the convection extent is satisfactory (e.g., whether there is low or no backflow). If the convection extent is not satisfactory, the method continues to step 70 in which the viscosity of the composition is increased as further detailed hereinabove. From step 70 the method loops back to step 64.

If, on the other hand the convection extent is satisfactory, the method proceeds to step 71 in which a region containing the tissue contacting the catheter is imaged by MRI, preferably T2-weighted and/or diffusion-weighted MRI, immediately after or several hours (e.g., 24 hours) post treatment. The method then continues to step 72 in which non-specific cytotoxic tissue response is assessed based on the images acquired in step 71. The method then proceeds to decision step 74 in which the methods determines whether or not the non-specific toxicity is low. If the non-specific toxicity is not low, the method continues to step 76 in which the composition is reformulated by manipulating the drug solvents or other physical, chemical, biological characteristics of the composition to decrease the cytotoxicity. From step 76 the method loops back to step 64, in which the above method steps are executed for an additional group of animals.

If, the non-specific toxicity is low (e.g., it cannot be reduced by a reasonable number, say 5-10 iterations or more) the method ends at step 80

An exemplified protocol for formulation of composition for CED is provided in the Examples section that follows.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container and labeled for treatment of an indicated condition, as further detailed above.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Example 1

In accordance with various exemplary embodiments of the present invention, rats subjected to CED treatment in the brain were imaged by MRI. The MR images were analyzed and used to monitor the convection of the administrated agent and to determine the cytotoxic response of the treated tissue.

Methods

Experiment Design

Solutions containing combinations of Cremaphore, Taxol®, Carboplatin, Ethanol, sucrose and human serum albumin (HSA) in different concentrations were mixed with Gd-DTPA (1:70). The resultant solution was infused into the striatum of normal Sprague-Dawley (SD) rats (males, 250-300 grams). T1-weighted MR images were acquired immediately post treatment to assess the extent of convection. Additionally, T2-weighted and diffusion-weighted MR images were acquired 24 hours post treatment to assess the response of the tissue and its correlation to the extent of convection. Some rats were monitored by MRI for an additional period of several days to demonstrate the subsequent formation of necrosis following the earlier changes observed on T2-weighted and diffusion-weighted MRI.

CED Procedure

Under full anesthesia, a midline scalp incision was made to identify the bregma. A 1 mm burr hole was made in the right region of the skull, 3 mm anterior and 2 mm lateral to the bregma. A 33-gauge needle attached to a 1000 μl syringe (Gastight; Hamilton) was placed stereotactically 5.5 mm deep into the striatum. The infusion was performed using a BASI syringe pump at a rate of 1 μl/min for a duration ranging from 17 to 90 min.

In order to verify that T1-weighted MR images, acquired immediately post treatment, represent the true distribution of the agent in the tissue, 11 rats were treated by CED with a composition containing 0.1% Evans Blue and Gd-DTPA (1:70) for 30 minutes. 7 out of these 11 rats were treated with a composition having higher viscosity, obtained by adding sucrose at a concentration of 17%. T1-weighted MRI were acquired immediately post treatment, after which the brains were extracted and fixated in Formalin. The relation between the volume of the immediate Gd-DTPA enhancement and the volume of the Evans Blue distribution in the fixated rat brain was studied.

In order to study the correlation between the extent of CED as depicted in the immediate T1-weighted images and the cytotoxic tissue response as depicted in the later diffusion-weighted MR images, 9 SD rats were treated by CED of Taxol® (0.54 mg/ml). In order to obtain a wide range in volumes of distribution, the infusion times were varied between 17 to 60 minutes. 13 rats were treated with Carboplatin (4 mg/ml, 17 minutes infusion). In order to obtain a wide range in volumes of distributions, in 6 out of those, the composition viscosity was increased by adding sucrose to the solution prior to infusion (Carboplatin 4 mg/ml, sucrose concentration-12%).

In order to study the tissue response to non-toxic agents, 13 rats were treated with several concentrations of human serum albumin (0.2%, 1.0% and 2.5%) and 12 rats with sucrose (5% and 20%) for a duration of 90 minutes.

Imaging

Immediate monitoring of CED formation and extent was performed using T1-weighted images obtained by a General Electric™ 0.5 T interventional MRI machine [Signa SP/i (special proceeding/interventional)] with 1× operating system and gradients intensity of up to 1 Gauss/cm. The T1-weighted images were acquired with: 256×128 matrix, 12×9 cm² field of view (FOV), repetition time (TR) of 400 ms, echo time (TE) of 12 ms and 3 mm slices with no gap.

Early assessment of tissue response was performed using diffusion-weighted and T2-weighted MR images. The diffusion-weighted images were obtained by acquiring conventional T2-weighted images with the addition of diffusion-weighting gradients that filter out the signal from high mobility water molecules and sensitize the MR images to molecular diffusion/mobility [Stejskal et al. supra]. Regions of accumulated liquids or severe necrosis appear dark in diffusion-weighted MRI, while regions of slow water accumulation, such as in the case of intracellular water accumulation or inflammation, appear brighter.

The diffusion-weighted and T2-weighted MR images were obtained by a General Electric™ 3.0 T MRI machine with 10.4M 1× operating system, gradients intensity of up to 4.3 Gauss/cm and line scan diffusion-weighted imaging [Gudbjartsson et al., "Line scan diffusion imaging", Magn. Reson. Med. 36:509-519, 1996] acquisition software package. Specially designed animal volume coils of 5 cm diameter were used for data acquisition.

The T2-weighted fast spin echo (FSE) MR images were acquired with: 256×128 matrix, FOV=12×9 cm², TR=3000 ms, TE=90 ms, and 2 mm slices with 0.5 mm gap.

The line-scan diffusion-weighted MR images were acquired with: 256×128 matrix, FOV=12×9 cm², TR=5440 ms, TE=142 ms and 2 mm slices with 0.5 mm gap. The diffusion-weighted MR images were acquired at diffusion weighting factor b of b=5 sec/mm$^2$ and 1000 sec/mm$^2$.

Image Processing

The volume (in cm$^3$) of the composition distribution was calculated from the T1-weighted MR images acquired immediately post CED treatment. Region-of interests (ROIs) were defined over the entire enhancing region in each slice (excluding the ventricles). The number of pixels in the ROIs was counted and multiplying by the volume of a single pixel. Equation 1 was used to calculate ADC maps of the diffusion-weighted MR images.

Viscosity Increment

Eight groups of rats (4-7 rats in each group) were treated by CED with compositions prepared, in accordance with preferred embodiments of the present invention with different viscosity values. The compositions were: (i) saline, (ii) HSA 0.2%, (iii) HSA 1%, (iv) sucrose 5%, (v) ethanol 5.5%, (vi) HSA 2.5%, (vii) Taxol 0.66 mg/ml, and (viii) sucrose 20%. All compositions were mixed with Gd-DTPA (1:70) prior to infusion.

The infusion time was 90 minutes. The viscosities were measured at room temperature using a W. Oswald viscosity meter and their values were expressed in relative to the saline solution. T1-weighted MR images taken immediately after treatment were used to determine CED efficacy for each of the 8 compositions. The final convection volume for each treatment was defined as the convection volume averaged over the respective group of rats.

The effect of the increased viscosity on the later stages was investigated by treating 13 rats with Carboplatin (4 mg/ml, 17 minutes infusion). Six rats were treated with a composition having increased value of viscosity. The viscosity was increased by adding sucrose at a concentration of 12% to the solution prior to infusion. All compositions were mixed with Gd-DTPA (1:70) prior to infusion. The rats were imaged immediately post infusion by axial T1-weighted MRI, 24 hours post infusion by diffusion-weighted MRI, and 4 days post infusion by T1-weighted MRI.

Results

Convection Monitoring

The extent of convection formation was reflected by T1-weighted MR images acquired immediately post infusion with infusates mixed with Gd-DTPA. Poor convection was characterized by significant backflow along the catheter and into the ventricles, depicted in the images as significant enhancement in the ventricles and little/no enhancement in the striatum. Efficient convection presented significant spread into the striatum with minimal backflow into the ventricles.

Reference is now made to FIGS. 3A-H which demonstrate the ability of the present embodiments to monitor convection during direct convective interstitial infusion.

FIGS. 3A-B are T1 and T2-weighted axial MR images of normal rat brain. FIGS. 3C-E show T1-weighted MRI acquired immediately post CED treatment with infusates containing Gd-DTPA and Evans Blue. FIGS. 3C-E demonstrate different convective efficiency as depicted by MRI: poor (FIG. 3C), moderate (Figure D) and efficient (Figure E) convection.

FIGS. 3F-H show fixated brain samples of the same rats of FIGS. 3C-E, demonstrating similar distributions of the Evans Blue dye in the tissue.

A highly significant correlation ($R^2$=0.95, p<0.0001, Pearson correlation) was found between the volume of the immediate Gd-DTPA enhancement (see FIGS. 3C-E) and the volume of the Evans Blue distribution (FIGS. 3F-H). The correlation between the two volumes of distribution was found to be highly significant.

FIGS. 4A-B are axial T1-weighted MR images acquired immediately post infusion of 5% (FIG. 4A) and 20% (FIG. 4A) sucrose solutions. The solutions were mixed with Gd-DTPA (1:70) prior to infusion. As shown in FIGS. 4A-B, the efficiency of convection, higher convection extent were obtained for the 20% sucrose solution, demonstrating that higher viscosity enables higher convection extent.

FIG. 5 shows the convection efficacy as a function of the relative viscosity. The convection efficacy was calculated from T1-weighted images of the respective groups and is expressed in terms of CED volume measured in cubic centimeters. The compositions numerals (i)-(viii) are designated near the data points in FIG. 5. The images were acquired immediately post CED treatment.

A significant correlation ($R^2$=0.79, p<0.003) was found between the viscosity and the convection efficacy, implying that compositions with low viscosity tend to form poor convection while compositions with high viscosity form efficient convection.

Table 1 summarizes the CED efficacy for compositions (i)-(viii).

TABLE 1

| Composition | relative viscosity | number of rats | CED VOLUME per group |
|---|---|---|---|
| saline | 1.00 | 6 | 0.024 ± 0.011 |
| HSA 0.2% | 1.04 | 6 | 0.048 ± 0.010 |
| HSA 1% | 1.11 | 4 | 0.052 ± 0.005 |
| sucrose 5% | 1.15 | 7 | 0.058 ± 0.011 |
| Ethanol 5.5% | 1.19 | 4 | 0.053 ± 0.021 |
| HSA 2.5% | 1.25 | 4 | 0.060 ± 0.015 |
| Taxol 0.66 mg/ml | 1.40 | 6 | 0.069 ± 0.004 |
| sucrose 20% | 1.70 | 5 | 0.097 ± 0.009 |

Determination of Cytotoxic Response

Efficient convection with toxic infusates were followed by significant enhancement in T2-weighted and diffusion-weighted MR images acquired 24 hours post treatment. Efficient prolonged (90 minutes) CED of non-toxic infusates, such as sucrose and human serum albumin solutions, was followed by minor enhancement on T2-weighted and diffusion-weighted MR images, at the site of the catheter tip. When convection was not achieved, including with toxic infusates, no changes were detected on the later T2-weighted and diffusion-weighted MR images.

FIGS. 6A-C are diffusion-weighted MR images acquired for cases of efficient convection, 24 hours post treatment. Shown in FIGS. 6A-C are diffusion-weighted MR images for rats treated with Taxol® (FIG. 6A), Cremaphore (FIG. 6B) and Carboplatin (FIG. 6C). As shown in FIGS. 6A-C efficient convection is followed by significant enhancement in diffusion-weighted MR images.

FIG. 7A is a T1-weighted MR image, acquired immediately following the CED of Taxol® mixed with Gd-DTPA. The bright area corresponds to Taxol® distribution in the rat striatum. As shown in shown in FIG. 7A the Taxol® was efficiently distributed over a large area of the striatum.

FIGS. 7B-C are T2-weighted and diffusion-weighted MR images of the same rat as FIG. 7A, acquired 24 hours post treatment. The contrast enhancement corresponds to the cytotoxic response of the tissue to the distributed Taxol®.

FIG. 7D is a low-power magnification of an en block-resected lesion taken from the same rat brain as FIGS. 7A-C. The brain was extracted immediately after the last MR scan.

Severe damage covering most of the striatum is seen with widespread necrosis and early gliotic changes. As shown in FIG. 7D the damaged region correlates with the bright regions of the T2-weighted and diffusion-weighted MR images of FIG. 7B-C, thus demonstrating the ability of determining the cytotoxic response of the tissue by MRI.

FIGS. 8A1-A3 are T1-weighted MR images acquired immediately post treatment with Gd-DTPA (catheter position marked in black). FIGS. 8B1-D3 are T1-weighted (FIGS. 8B1-B3), T2-weighted (FIGS. 8C1-C3) and diffusion-weighted (FIGS. 8D1-D3) MR images acquired 24 hours post treatment. FIGS. 8A1, 8B1, 8C1 and 8D1 demonstrate poor convection with 0.2% human serum albumin, no toxicity; FIGS. 8A2, 8B2, 8C2 and 8D2 demonstrate efficient convection with 17% sucrose, minimal toxicity; and FIGS. 8A3, 8B3, 8C3 and 8D3 demonstrate efficient convection with Taxol®, severe tissue toxicity.

As shown in the T1-weighted MR images, there is no residual Gd-DTPA in the brain. As shown in the T2-weighted and diffusion-weighted MR images, various tissue cytotoxic responses were observed.

Reference is now made to FIGS. 9A-C which demonstrate the relation between the volume of the Gd-DTPA enhancement and the volume of cytotoxic tissue response as studied for the 9 Taxol® treated rats. The Gd-DTPA enhancement was determined from T1-weighted MRI taken immediately post treatment and the cytotoxic tissue response was determined from diffusion-weighted MR images taken later, as further detailed above (see Methods).

FIG. 9A is T1-weighted MR image acquired immediately post treatment of one rat with the admixture of Taxol® and Gd-DTPA; FIG. 9B is diffusion-weighted MR image of the same rat acquired 24 post treatment; and FIG. 9C is a correlation graph, showing, on the abscissa, the enhancement volume in $cm^3$ as calculated for 9 rats treated with CED of Taxol® from the MR images similar to that of FIG. 9B, and on the ordinate the enhancement volume in $cm^3$ as calculated from images of the same 9 rats similar to that of FIG. 9A. Significant correlation was found between the two enhancement volumes (Taxol®: $R^2=0.75$, $p<0.004$; Carboplatin: $R^2=0.67$, $p<0.002$, Pearson correlation), demonstrating the ability of the present embodiments to monitor the convection by T1-weighted MRI and determine the cytotoxic response by diffusion-weighted MRI.

FIGS. 10A-F are MR images of cases treated with Carboplatin solution (4 mg/ml) (FIGS. 10A, 10C, 10E) and with the addition of 12% sucrose (FIGS. 10B, 10D, 10F). The MR images are: axial T1-weighted MR images acquired immediately post infusion (Figures A-B), diffusion-weighted MR images acquired 24 hours post infusion (Figures C-D), and T1-weighted MR images acquired 4 days post infusion (Figures E-F). As shown in FIGS. 10A-F, the efficacy and extent of the convection are higher for the more the viscous solution (FIGS. 10B, 10D, 10F). The diffusion-weighted and T1-weighted MR images acquired 24 hours and 4 days post treatment demonstrate larger extent of toxic tissue response when the to the more viscous solution.

Discussion

In the present examples the application of MRI for monitoring convection as well as determining cytotoxic response of cells to CED was demonstrated. CED formation and extent was monitored by T1-weighted MRI and cytotoxic tissue response was determined by T2-weighted and diffusion-weighted MRI.

Gd-DTPA has been previously used as a surrogate marker for CED distribution, by chemically binding or entrapping it to macromolecules or other particles such as liposomes and co-infusing the labeled particles with the original infusate (Saito et al., supra; Mamot et al., supra; Nguyen et al., "Convective distribution of macromolecules in the primate brain demonstrated using computerized tomography and magnetic resonance imaging", J Neurosurg, 98(3):584-90, 2003; and Lonser et al., "Successful and sage perfusion of the primate brainstem: in vivo MRI of macromolecular distribution during infusion", J Neurosurg, 97:905-913, 2002]. Gd-DTPA has also been used to monitor the extent of CED with saline [Weber et al., abstract RA-24, Eighth Annual Scientific Meeting of the Society for Neuro-Oncology, Keystone, Colo., November 2003, SNO 2003.

Attempts have also been made to perform real-time in vivo CT imaging of convection using small radioactive imaging tracer [Croteau et al., J. Neurosurg 102:90-97, 2005]. However, although the use of CT for real-time monitoring of CED is problematic because (i) CT has a relatively low anatomical resolution compared to MRI, and (ii) CT can not be used for multiple imaging sessions due to accumulation of radiation.

The present embodiments successfully monitor therapeutic agents convection within tissues by co-formulating (e.g., mixing) the therapeutic agents with an MRI contrast agent (e.g., Gd-DTPA) prior to infusion, and imaging the tissue, contemporaneously, immediately post infusion or at a later time. Such procedure can provide real-time assessment of formation efficiency and extent of CED. The significant correlation between the extent of CED, as depicted by the immediate T1-weighted images, and the distribution of the Evans Blue dye (similar molecular weight to Taxol) in the fixated rat brain samples, as well as the significant correlation with the later cytotoxic tissue responses, as depicted by the DWMR images, in the cases of Taxol and Carboplatin, confirms the validity of the present embodiments.

Since Gd-DTPA is a small particle, it is carried along with the convective wave of the therapeutic agents. Short clearance time of Gd-DTPA from the tissue was observed in 3 cases. For these cases, sequential T1-weighted MR images showed clearance of significant percentage of the Gd-DTPA within 2-4 hours post infusion (data not shown). It is assumed that for larger molecules the clearance time is longer.

Early assessment of tissue cytotoxic response to treatment is essential, especially in the case of brain tumors, where both efficient treatments of pathological regions as well as sparing of normal tissue are critical. Accurate non-invasive treatment monitoring can enable treatment adjustment in real-time thus optimizing treatment outcome on a patient by patient basis.

The non-specific cytotoxic tissue response, depicted as enhancing regions on T2-weighted and diffusion-weighted MR images, is consistent with previous clinical findings obtained by the present Inventors [Mardor et al; Lidar et al., supra], where data of 15 patients with recurrent GBM treated by CED of Taxol® were presented. This clinical data showed that early changes in the diffusion-weighted MR images were followed by later tumor necrosis. Patients who did not present early changes on the diffusion-weighted MR images had no later radiological responses to treatment. On the other hand, Mardor et al. and Lidar et al. fail to identify the reason for the early changes in the diffusion-weighted MR images. In particular, Mardor et al. and Lidar et al. fail to correlate enhancement in diffusion-weighted MR images with tissue cytotoxic response.

The finding presented in the present example and obtained in accordance with various exemplary embodiments of the present invention, successfully provide clarification as to the reason of the early changes observed by Mardor et al. and Lidar et al. Specifically, the present embodiments allow the identification of enhancement regions in diffusion-weighted MR images with the tissue cytotoxic response to the Taxol®. Moreover, the explanation for no response in some of the patients in Lidar's clinical trial is the lack (or low efficiency) convection and consequently small distribution volume of Taxol® in the tissue.

Efficient prolonged (90 minutes) CED of non-toxic infusates, was followed by minor enhancement on T2-weighted and diffusion-weighted MR images, at the site of the catheter tip. This minor damage to the tissue can be explained by the large pressure gradient caused by the continuous infusion. This finding is consistent with the calculations by Chen et al. [Chen et al., "Intraparenchymal drug delivery via positive-pressure infusion: experimental and modeling studies of poroelasticity in brain phantom gels", IEEE Transactions on Biomedical Engineering, 49(2):85-96, 2002], which showed that for long infusion times the pore fraction increases at short radial distances from the catheter tip.

The present animal study demonstrates the ability of MRI to determine cytotoxic tissue response. Diffusion-weighted MRI is somewhat advantageous over T2-weighted MRI since it provides additional information (see FIGS. 8A-H). Diffusion-weighted MRI is particularly advantageous for the detection of cytotoxic tissue response in brain tumors, because most brain pathologies are accompanied by vasogenic edema which appears bright in T2-weighed MR images. The heterogeneous appearance of pre-treatment pathology, in addition to vasogenic brain edema, may screen the T2 changes resulting from the treatment. In diffusion-weighted MRI, on the other hand, most of the signal from vasogenic edema is filtered out, thus making this technique more effective than T2-weighted MRI, at least for the detection of cytotoxic tissue response in brain tumors.

Additionally, the present study demonstrates that the increasing the viscosity of the composition significantly enhances the efficiency of convection-based treatments both in terms of the convection (extent, distribution) and in terms of the response of the tissue to the treatment.

Example 2

In accordance with various exemplary embodiments of the present invention, high viscosity infusates were used for distributing Iron Oxide (IO) nano particles in rat brain by CED.

Methods

The impact of enhanced viscosity on CED of large particles was tested for 10 nano-particles (20 nm dry size, 70 nm wet size).
Experiment 1
A low viscosity solution consisting of IO biocompatible and biodegradable particles suspended in saline and a high viscosity solution, consisting of the same concentration of IO particles, suspended in a saline solution containing HSA were infused into the rat striatum. The infusion was performed at a rate of 1 µl/min for duration of 30 minutes. Immediate monitoring of CED formation and extent was performed using gradient echo MR images.
Experiment 2
IO particles, as in Experiment 1 were covered with Dextrane to increase viscosity and infused into rat brain. The infusion was performed at a rate of 4 µl/min for duration of 15 minutes. 24 rats were scanned immediately post treatment by MRI and 5 were followed by MRI for 4 weeks. One rat was treated with concentration of 0.2 mg/ml for 7.5 minutes at a rate of 8 µl/min. Two rats were treated with a high concentration infusate (2 mg/ml), and subsequently their brains were harvested to assess IO distribution by direct visualization. Three rats were treated with a low IO concentration (0.05 mg/ml) in a 20% sucrose solution to increase viscosity. Eight rats were treated by IO particles labeled by Rhodamine B Amine, and subsequently the brains were harvested and evaluated by MRI and spectral imaging.

Results

Experiment 1
FIGS. 11A-B show Sagittal slices of gradient echo MRI acquired immediately post infusion with the low viscosity IO infusate (2 rats, FIG. 11A) and the high viscosity IO infusate (2 rats, FIG. 11B). The presence of IO particles is shown in the gradient echo MR images as a dark region near the catheter tip.

As shown in FIGS. 11A-B, although the two solutions (low and high viscosity) had an identical number of IO particles, the CED of the low viscosity IO infusate resulted in a dark region which is significantly smaller (about 1-2 mm in diameter) compared to the artifact caused by using the viscous infusate (4 mm diameter). It is therefore demonstrated that the efficacy and extent of convection strongly depends on the viscosity of the infused composition.
Experiment 2
FIGS. 12A-D show gradient-echo MR images taken immediately post treatment with a 0.2 mg/ml infusate at 8 µl/min over 7.5 minutes (FIG. 12A); gradient-echo MR images taken immediately post treatment with a 0.2 mg/ml infusate at 4 µl/min over 15 minutes (FIG. 12B); direct visualization of a brain harvested immediately post treatment with the high concentration infusate (FIG. 12C); and spectral image taken immediately post treatment by the fluorescent-labeled IO.

Figure 12A:
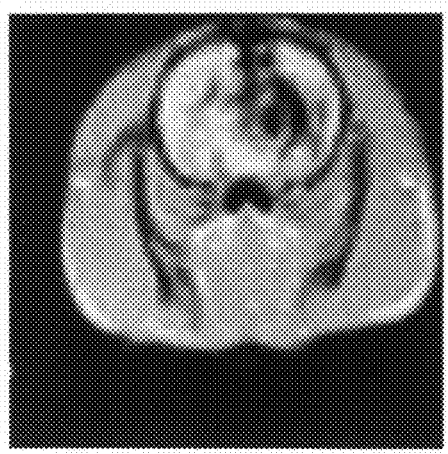
Figure 12B:
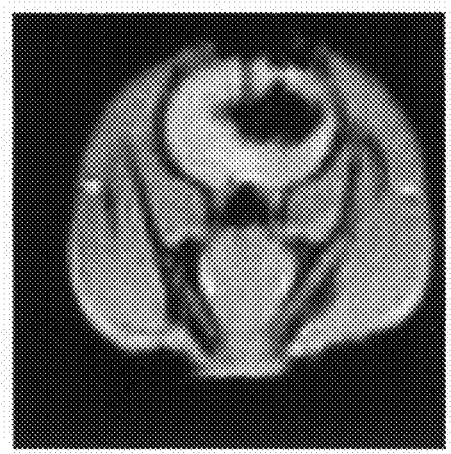
Figure 12C:
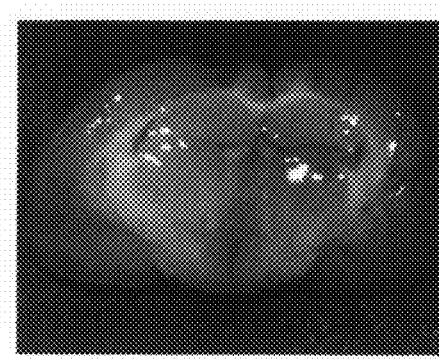
Figure 12D:
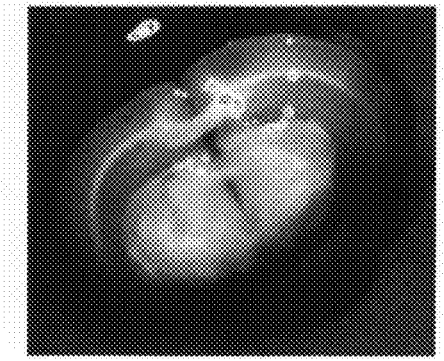
Figure 13A:
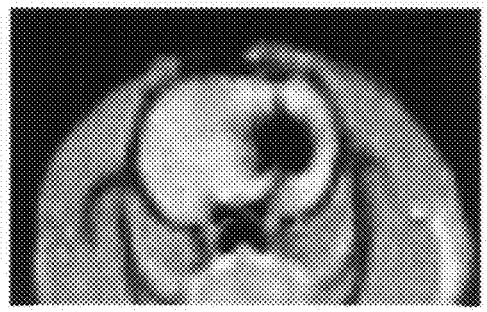
Figure 13B:
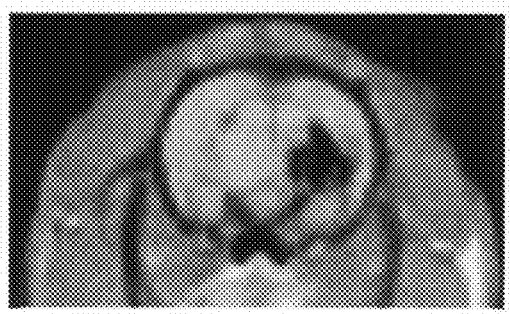
Figure 13C:
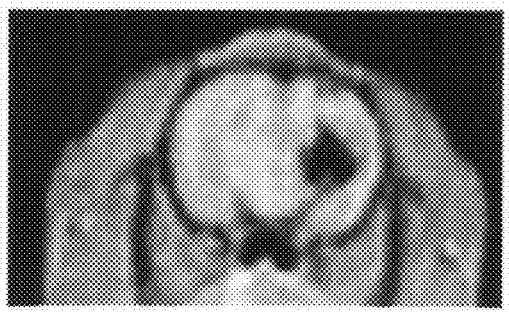
Figure 13D:
Figure 14A:
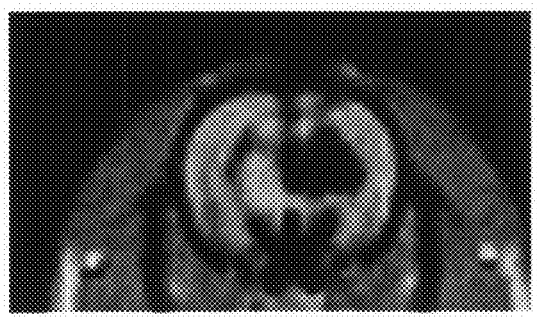
Figure 14B:
Figure 14C:
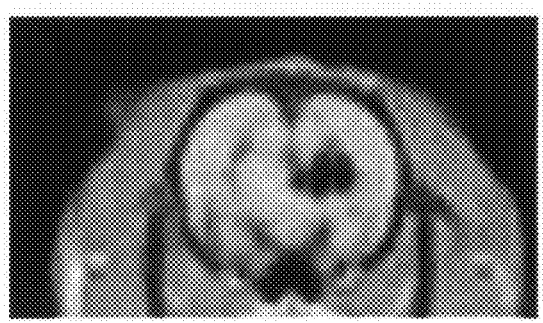
Figure 14D:
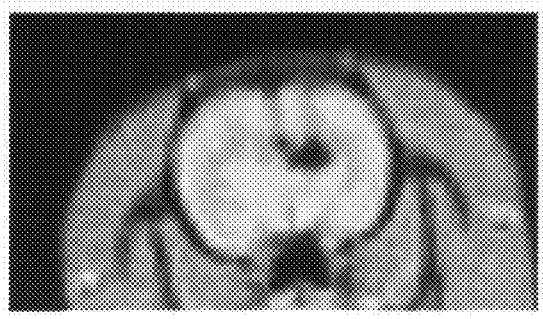

As shown in FIG. 12A the treatment with 0.2 mg/ml infusate at 8 µl/min over 7.5 minutes, resulted in poor CED which was observed as backflow of the IO particles into the ventricles as shown in FIGS. 12B-D, the other treatments resulted in efficient CED observed as homogenous distribution of IO in the striatum.

FIGS. 13A-D and FIGS. 14A-D show gradient-echo MR images taken for rat Nos. 1 (FIGS. 13A-D) and 2 (FIGS. 14A-D), immediately (FIGS. 13A and 14A), 3 days (FIGS. 13B and 14B), 6 days (FIGS. 13C and 14C) and 27 days (FIGS. 13D and 14D) post the CED treatment with a 0.2 mg/ml infusate at 4 µl/min over 15 minutes.

The maximal distribution reached was 31.4 mm². The long-term follow-up showed near linear clearance of the particles, reaching 20-40% of the original distribution after 4 weeks. No toxicity was detected. In the fluorescent and the direct IO visualization studies the distribution areas were 7.8 and 8.2 mm², respectively (see FIGS. 12C-D).

FIGS. 15A-C show gradient-echo MR images taken for rat Nos. 1, 2 and 3, respectively, immediately post treatment with low concentration IO (0.05 mg/ml) in the 20% sucrose solution at infusion rates of 1 µl/min over 30 minutes (FIGS. 15A-B), and 2 µl/min over 15 minutes (FIG. 15D). As shown, the sucrose in the low concentration infusate caused aggregation of the IO particles resulting in no penetration of the IO into the tissue.

The present example demonstrates that the high viscosity of the infusates, according to the teaching of the present embodiments, enables a rapid (15 mints infusion time) and efficient distribution of large particles via CED. The clearance time of the large particles was significantly longer than that of small particles. Additionally, the present example demonstrates the use of MR imaging for real time direct depiction of IO distribution.

Example 3

In accordance with various exemplary embodiments of the present invention, high viscosity infusates were used for distributing high viscosity toxic infusates in mice thigh.

Methods

Five balb-c mice, bearing large (over 2 cm in diameter) C26 colon cancer tumors in the thigh, were treated with CED of high viscosity toxic infusates. Three mice were treated with high concentration Paclitaxel (1.2 mg/ml) at infusion rate of 4 µl/min for 60 minutes. Two mice were treated with a high concentration combination of Ethanol and Cremaphore (150 µl Ethanol and 150 µl Cremaphore diluted with Saline to 1 ml) at infusion rate of 4 µl/min for 105 minutes.

Infusates were mixed with Gd (1:70) prior to treatment. MR images were acquired immediately post treatment to assess the distribution of the drug within the tumor. The mice treated with Paclitaxel were rescanned 24 hours post treatment to assess tissue response.

Results

FIGS. 16A-H: show an example of a large C26 tumor induced in the thigh of a balb-c mouse treated by CED of high concentration Paclitaxel: FIGS. 16A-B are T2 MR images of the tumor prior to treatment; FIGS. 16C-D are T1 MR images taken immediately post treatment; FIGS. 16E-G are T2 MR images taken 24 hours post treatment; and FIG. 16H is an image of the treated mouse.

The Gd-enhanced shown in FIGS. 16C-D depicts the efficient distribution of the drug in the tumor during the CED treatment. The maximal distribution diameter was about 1.4 cm. As shown in the 24 hours follow-up (FIG. 16E-G), the high Paclitaxel concentration and effective distribution has caused complete necrosis of the tumoral tissue in regions treated by CED within 24 hours or less.

Similar results were obtained for the other mouse the Ethanol/Cremaphore combination.

FIGS. 17A-M show an example of a large C26 tumor induced in the thigh of a balb-c mouse treated by CED of high concentration Paclitaxel: FIGS. 17A-D are T2 MR images of the tumor prior to treatment; FIG. 17E-H are T1 MR images taken immediately post treatment; FIG. 17(I)-L are T2 MR images taken 24 hours post treatment; and FIG. 17M is an image of the treated mouse.

As shown in FIG. 17E-H, a considerable, nearly complete backflow of the drug was observed, revealing inefficient CED. As shown in the 24 hours follow-up there was no significant change in the tumor indicating that the treatment was not effective.

Example 4

In accordance with various exemplary embodiments of the present invention, rats were treated with high viscosity infusates containing blue bovine serum albumin and Gd-DTPA by CED.

Methods

Ten rats were treated by CED with an infusate containing 1.0% blue bovine serum albumin (40 KD) and Gd-DTPA (1:70) at infusion rate of 4 µl/min for 20 minutes. Four out of the ten rats were treated with a higher viscosity infusate obtained by adding human serum albumin at a concentration of 2%. T1-weighted MRI were acquired immediately post treatment, after which the brains were harvested and fixated in Formalin.

Results

FIGS. 18A-B through FIGS. 22A-B are the T1-weighted MR images acquired immediately post treatment (A) and respective optical images of the tissue samples (B) of five different rats. The correlation between the area of Gd distribution, as depicted in the immediate T1 MR images, and the area of distribution as depicted in the tissue samples was found to be highly significant ($r^2$=0.92, p<0.0001, Pearson correlation). The significant correlation expresses the ability of the present embodiments to monitor CED extent for lager molecules.

Example 5

Following is an exemplified protocol for formulating a composition for CED. Different solvents were used for dissolving Taxol so as to test for non-specific neurotoxicity. The different solvents were prepared from different combinations of drugs selected from the group consisting of Peg 8000, Tween 80, DMSO, Cremaphore, Ethanol, Saline and Gd-DTPA were used in CED.

For each solvent, immediate monitoring of CED formation and extent was performed using T1-weighted images, and assessment CED toxicity was performed using T2-weighted MR images.

FIGS. 23A-H are T1-weighted MR images acquired immediately post treatment (FIGS. 23A-D) and respective T2-weighted MR images acquired 24 hours post treatment (FIGS. 23E-H). The MR images demonstrate moderate toxicity (FIGS. 23A and 23E, FIGS. 23B and 23F), minor toxicity (FIGS. 23C and 23G) and no toxicity (FIGS. 23D and 23H).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:
1. A method of administering a pharmaceutical agent to a tissue by direct convective interstitial infusion, the method comprising:

placing at least one direct convective interstitial infusion catheter in contact with the tissue;

pressuring said pharmaceutical agent in a liquefied form having a viscosity being X times larger than a viscosity of saline through said at least one direct convective interstitial infusion catheter, wherein said pressuring is characterized by a flow rate selected to induce interstitial convection of said liquefied form, wherein said X is from about 1.04 to about 1.7.

2. The method of claim 1, wherein said pressuring said pharmaceutical agent is characterized by a flow rate larger than 4 microliters per minute, and is executed while substantially minimizing backflow of said pharmaceutical agent along an outer wall of said at least one direct convective interstitial infusion catheter.

3. The method of claim 1, wherein the tissue is a tumor.

4. The method of claim 1, wherein the tissue is a brain tumor.

5. The method of claim 1, wherein the tissue is a brain pathology.

6. The method of claim 1, wherein the tissue is a spine pathology.

7. The method of claim 1, wherein the tissue is a prostate pathology.

8. The method of claim 1, wherein the tissue is a pancreas pathology.

9. The method of claim 1, wherein the tissue is a kidney pathology.

10. The method of claim 1, wherein the tissue is a liver pathology.

11. The method of claim 1, wherein said pharmaceutical agent comprises a therapeutic agent.

12. The method of claim 11, wherein said therapeutic agent has a molecular weight of at least 200 kDa.

13. The method of claim 1, wherein said pharmaceutical agent in said liquefied form comprises a nanoparticle.

14. The method of claim 1, wherein said pharmaceutical agent in said liquefied form comprises a liposome.

15. The method of claim 1, wherein said pharmaceutical agent in said liquefied form comprises stem cells.

16. The method of claim 1, wherein said pharmaceutical agent in said liquefied form comprises macrophages.

17. The method of claim 1, wherein said pharmaceutical agent comprises a diagnostic agent.

18. The method of claim 17, wherein said diagnostic agent comprises an MRI contrast agent.

19. The method of claim 18, wherein said MRI contrast agent has a T1 shortening effect.

20. The method of claim 1, wherein said viscosity value is equal to a viscosity of human serum albumin at a concentration of about 0.2%.

21. The method of claim 1, further comprising imaging a region containing the tissue by MRI thereby providing at least one image of said region.

22. The method of claim 21, further comprising using said at least one image for monitoring the convection of said pharmaceutical composition within the tissue.

23. The method of claim 21, further comprising dissolving or dispersing an MRI contrast agent in said pharmaceutical composition.

24. A method of administering a pharmaceutical composition to a tissue by direct convective interstitial infusion, the pharmaceutical composition being in a liquid form, the method comprising:

placing at least one direct convective interstitial infusion catheter in contact with the tissue;

increasing a viscosity of the pharmaceutical composition to a viscosity value being X times larger than a viscosity of saline, wherein said X is from about 1.04 to about 1.7; and pressuring the pharmaceutical composition through said at least one direct convective interstitial infusion catheter, wherein said pressuring is characterized by a flow rate selected to induce interstitial convection of said liquid form.

25. The method of claim 24, wherein said predetermined value is selected so as to allow pressuring of the pharmaceutical composition at a flow rate larger than 4 microliters per minute, while substantially minimizing backflow of said pharmaceutical agent along an outer wall of said at least one direct convective interstitial infusion catheter.

26. A direct convective interstitial infusion method, comprising:

providing a pharmaceutical composition which comprises a therapeutic agent and an MRI contrast agent, the pharmaceutical composition being in liquid form and having a viscosity being X times larger than a viscosity of saline, wherein said X is from about 1.04 to about 1.7;

pressuring said pharmaceutical composition through at least one direct convective interstitial infusion catheter into an interstitial volume of a tissue, wherein said pressuring is characterized by a flow rate selected to induce interstitial convection of said liquid form;

imaging a region containing the tissue by MRI thereby providing at least one image of said region; and using said at least one image for monitoring the convection of said therapeutic agent within the tissue, wherein said monitoring the convection comprises detecting backflow of said pharmaceutical composition along said at least one direct convective interstitial infusion catheter.

27. The method of claim 26, wherein said MRI contrast agent is selected so as to allow convection of said MRI contrast agent together with said therapeutic agent, while prolonging a time in which said MRI contrast agent remains in the tissue.

28. The method of claim 26, wherein said monitoring the convection comprises comparing the images with baseline images.

29. The method of claim 26, wherein said monitoring the convection comprises correlating intensity level of the images with level of presence of said therapeutic agent.

30. The method of claim 26, wherein said monitoring the convection comprises correlating intensity level of the images with a concentration of said therapeutic agent.

31. The method of claim 26, wherein said monitoring the convection comprises calculating distribution volume of said pharmaceutical composition.

32. The method of claim 26, wherein said monitoring the convection comprises calculating expansion rate of said pharmaceutical composition.

33. The method of claim 26, wherein said monitoring the convection comprises determining a direction of expansion of said pharmaceutical composition.

34. The method of claim 26, wherein said monitoring the convection comprises detection leakage of said pharmaceutical composition into low resistance paths.

35. The method of claim 26, further comprising providing diffusion-weighted or T2-weighted magnetic resonance images of said tissue, and using said diffusion-weighted or T2-weighted magnetic resonance images for determining the response of the tissue to the direct convective interstitial infusion.

36. The method of claim 35, wherein the response of the tissue comprises a cytotoxic response.

37. The method of claim 35, wherein the response of the tissue comprises a necrotic response.

38. The method of claim 35, wherein the response of the tissue comprises an inflammatory response.

39. The method of claim 35, wherein said determining the response of the tissue comprises calculating apparent diffusion coefficient (ADC) of the tissue and correlating said ADC with the response of the tissue.

40. The method of claim 39, wherein said determining the response of the tissue comprises generating an ADC map of the tissue and of neighboring tissues.

41. The method of claim 19, wherein said MRI contrast agent comprises a diethylenetriamine pentaacetic acid (DTPA).

42. The method of claim 19, wherein said paramagnetic metal comprises Gadolinium (Gd).

43. The method of claim 19, wherein said MRI contrast agent comprises Gadolinium-diethylenetriamine pentaacetic acid (Gd-DTPA).

44. A method of administering a pharmaceutical agent to a tissue by direct convective interstitial infusion, the method comprising:

placing at least one direct convective interstitial infusion catheter in contact with the tissue;

pressuring said pharmaceutical agent in a liquefied form having a viscosity which is equal to a viscosity of human serum albumin at a concentration of about 0.2% through said at least one direct convective interstitial infusion catheter, wherein said pressuring is characterized by a flow rate selected to induce interstitial convection of said liquefied form.

* * * * *